United States Patent
Bernotas et al.

(12)

(10) Patent No.: US 6,465,490 B1
(45) Date of Patent: Oct. 15, 2002

(54) SULFURIC ACID MONO-[3({1-[2-(4-FLUORO-PHENYL)-ETHYL]-PIPERIDIN-4-YL}-HYDROXY-METHYL)-2-METHOXY-PHENYL]ESTER

(75) Inventors: Ronald Charles Bernotas, Bridgewater, NJ (US); Paul Wayne Brown, Kansas City, MO (US); Gary Thomas Emmons, Washington, NJ (US); Chi-Hsin Richard King, Slingerlands, NY (US)

(73) Assignee: Aventis Pharmaceuticals Inc., Bridgewate, NJ (US)

( * ) Notice: Subject to any disclaimer, the term of this patent is extended or adjusted under 35 U.S.C. 154(b) by 0 days.

(21) Appl. No.: 09/615,246

(22) Filed: Jul. 13, 2000

Related U.S. Application Data

(60) Provisional application No. 60/198,215, filed on Jul. 16, 1999, now abandoned.

(51) Int. Cl.$^7$ ................... A61K 31/445; C07D 211/22
(52) U.S. Cl. ................... 514/317; 546/240; 546/241
(58) Field of Search ................... 514/317; 546/240, 546/241

(56) References Cited

U.S. PATENT DOCUMENTS

| | | | |
|---|---|---|---|
| 4,783,471 A | 11/1988 | Carr et al. | 514/317 |
| 4,877,798 A | 10/1989 | Sorensen et al. | 514/317 |
| 4,908,369 A | 3/1990 | Schechter et al. | 514/277 |
| 4,912,117 A | 3/1990 | Carr et al. | 514/317 |
| 5,021,428 A | 6/1991 | Carr et al. | 514/317 |
| 5,106,855 A | 4/1992 | McLees | 514/317 |
| 5,134,149 A | 7/1992 | Carr et al. | 514/317 |
| 5,169,096 A | 12/1992 | Carr et al. | 546/241 |
| 5,478,846 A | 12/1995 | Carr et al. | 514/330 |
| 5,561,144 A | 10/1996 | Carr et al. | 514/317 |
| 5,618,824 A | 4/1997 | Schmidt et al. | 514/317 |
| 5,700,812 A | 12/1997 | Carr et al. | 514/317 |
| 5,700,813 A | 12/1997 | Carr et al. | 514/317 |
| 5,721,249 A | 2/1998 | Carr et al. | 514/317 |
| 5,874,445 A | 2/1999 | Carr et al. | 514/317 |

OTHER PUBLICATIONS

Mathis et al. "Synthesis and preliminary in vivo evaluation of . . . " Med. Chem. Res. v.6, p. 1–10, (1996).*
Lundkvist et al. "Improved syntheses of the PET radioligands . . . " J. Label. Radiopharm. (1998) CLI 545–556.*
Sinkula et al. "Rationale for design of biologically reversible drug derivatives" J. Pharm. Sci. (1975) v.64, p. 181–210.*
Rose et al. "Metabolism of 5Ohydroxytryptamine o–sulfate in the rat" CA 75:17110 (1971).*
Doudet et al. "Distribution and kinetics of . . . " CA 116:2896 (1991).*
Wilson et al. "Texbook of organic medicinal and pharmaceuitcal chemistry" Lippincot co. (1977) p. 348–349.*
Munson et al. "Principles of pharmacology" Chapmann & Hall, (1995), p. 52–58.*
Yiyun Huang, et al: *J. Labelled Compd Radiopharm.* vol. 42, pp. 949–957 (1999).
J. Am. Soc. Mass Spectrom. (1997), 8(4), pp. 371–379, T.G. Heath, et al.
J. Pharm. Biomed. Anal. (1998), 17(1), pp. 17–25, D. Scott et al.
Tetrahedron Letters (1985), 26(2), pp. 123–126, Barry M. Trost, et al.
Synthetic Commun. (1991), 21(2), pp. 167–171, J. J. Landi, et al.
Tetrahedron, Asymmetry. (1992), vol.3, No. 12, pp. 1475–1504, S. Wallbaum, et al.

* cited by examiner

*Primary Examiner*—Ceila Chang
(74) *Attorney, Agent, or Firm*—Balaram Gupta; Joseph T. Strupczewski

(57) ABSTRACT

The present invention is directed to sulfuric acid mono-[3-({1-[2-(4-fluoro-phenyl)-ethyl]-piperidin-4-yl}-hydroxymethyl)-2-methoxy-phenyl]ester a metabolite of the $5HT_{2A}$ antagonist (+)-α-(2,3-dimethoxyphenyl)-1-[2-(4-fluorophenyl)ethyl]-4-piperidinemethanol and a processes for its preparation and its use in the treatment for a number of disease states.

86 Claims, No Drawings

US 6,465,490 B1

SULFURIC ACID MONO-[3({1-[2-(4-FLUORO-PHENYL)-ETHYL]-PIPERIDIN-4-YL}-HYDROXY-METHYL)-2-METHOXY-PHENYL]ESTER

This application claims the benefit of U.S. Provisional Application No. 60/198,215, filed Jul. 16, 1999 now ABN.

FIELD OF THE INVENTION

The present invention relates to a novel compound, its method of making, its method of use and intermediates thereof. It is a pharmaceutically active compound useful as an antagonist of serotonin at the $5HT_{2A}$ receptor. It is useful in treating conditions and diseases such as schizophrenia, anxiety, variant angina, anorexia nervosa, Raynaud's phenomenon, intermittent claudication, coronary or peripheral vasospasms, fibromyalgia, cardiac arrhythmias, thrombotic illness, controlling the extrapyramidal symptoms associated with neuroleptic therapy, depressive and bipolar disorders, obsessive-compulsive disorders, insomnia and sleep apnea.

BACKGROUND OF THE INVENTION (+)-α-(2.3-Dimethoxyphenyl)-1-[2-(4-fluorophenyl) ethyl]-4-piperidinemethanol has the following structure:

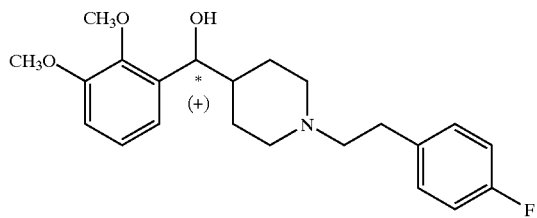

It is a novel pharmaceutically active compound in the treatment of conditions and diseases useful as an antagonist of serotonin at the $5HT_{2A}$ receptor, and as such, is useful in a variety of treatments such as schizophrenia, anxiety, variant angina, anorexia nervosa, Raynaud's phenomenon, intermittent claudication, coronary or peripheral vasospasms, fibromyalgia, cardiac arrhythmias, thrombotic illness, controlling the extrapyramidal symptoms associated with neuroleptic therapy, depression. bipolar disorders obsessive-compulsive disorders, insomnia and sleep apnea. α-(2,3-Dimethoxyphenyl)-1-[2-(4-fluorophenyl)ethyl]-4-piperidinemethanol has been generically described in U.S. Pat. No. 5,169,096, issued Dec. 8, 1992, the disclosure of which is incorporated herein by reference. (+)-α-(2,3-Dimethoxyphenyl)-1-[2-(4-fluorophenyl)ethyl]-4-piperidinemethanol was thereafter described in U.S. Pat. No. 5,134,149, issued Jul. 28, 1992, the disclosure of which is incorporated herein by reference. U.S. Pat. No. 5,700,813, issued Dec. 23, 1997, U.S. Pat. No. 5,700,812, issued Dec. 23, 1997, U.S. Pat. No. 5,561,144, issued Oct. 1, 1996, U.S. Pat. No. 5,721,249 issued Feb. 23, 1998 and U.S. Pat. No. 5,874,445 issued Feb. 23, 1999, the disclosure of each which is incorporated herein by reference, describe the use of (+)-α-(2,3-dimethoxyphenyl)-1-[2-(4-fluorophenyl)ethyl]-4-piperidinemethanol as $5TH_{2A}$ receptor antagonists in the treatment of a number of disease states as described above. Other U.S. Patents, which describe the use of the generic species in the treatment of a number of disease states, are U.S. Pat. Nos. 4,783,471; 4,877,798; 4,908,369; 4,912,117; 5,021,428; 5,106,855; 5,618,824 and U.S. Pat. No. 5,478,846, which generically discloses intermediates. Each of the preceding disclosures is incorporated herein by reference.

The compound of the present invention has been found to be an active metabolite of (+)-α-(2,3-dimethoxyphenyl)-1-[2-(4-fluorophenyl)ethyl]-4-piperidinemethanol by virtue of its ability to act as an antagonist at the $5TH_{2A}$ receptor and represents the major metabolite of (+)-α-(2,3-dimethoxyphenyl)1-[2-(4-fluorophenyl)ethyl]-4-piperidinemethanol found in plasma. The unsulfated version of the present invention (+)-α-(3-hydroxy-2-methoxyphenyl)-1-(2-(4-fluorophenyl)ethyl)-4-piperidinemethanol is also a metabolite of (+)-α-(2,3-dimethoxyphenyl)1-[2-(4-fluorophenyl)ethyl]-4-piperidinemethanol as described in Heath, T. G. et al. *J. Am. Soc. Mass Spectrom.* (1997), 8(4), 371–379, and Scott, D. et al. *J. Pharm. Biomed. Anal.* (1998), 17(1), 17, incorporated herein by reference. Even though the present invention is a mono sulfated conjugate of (+)-α-(3-hydroxy-2-methoxyphenyl)-1-(2-(4-fluorophenyl)ethyl)-4-piperidinemethanol, unexpectedly, according to tests described hereafter, it has been found to cross the blood-brain barrier and therefore may be useful in the treatment of central nervous system conditions or diseases which are treated by antagonizing the effects of serotonin at the $5TH_{2A}$ receptor.

It is an object of the present invention to provide a compound useful in treating a variety of diseases or conditions. This compound should have a binding profile (affinity or lack of affinity for specific receptors), which permits therapeutic activity without undue side effects. For example, too much affinity for the alpha1 receptor may result in orthostatic hypotension and sedation. Too much affinity for the dopamine 2 ($D_2$) receptor can result in hyperprolactinemia, extrapyramidal side effects (EPS) and tardive dyskinesia. Also, preferably the present invention should cross the blood-brain barrier in order to be active against diseases or conditions that affect the central nervous system. The present invention solves these problems by having an effective binding profile sufficient to treat certain diseases or conditions without significant side effects and treats certain central nervous systems diseases or conditions.

SUMMARY OF THE PRESENT INVENTION

The present invention is a compound of Formula I, II or III

Formula I

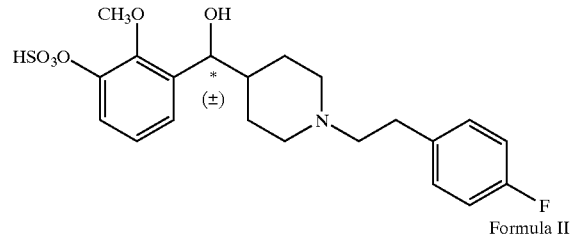

Formula II

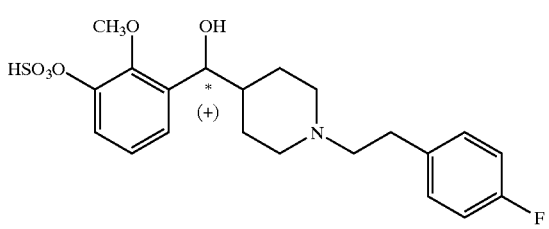

-continued

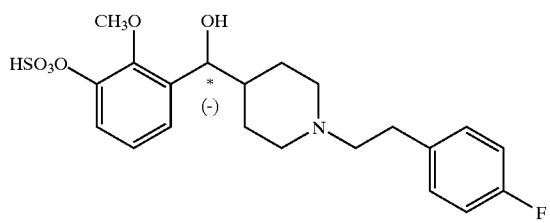

Formula III or a pharmaceutically acceptable salt thereof, and methods for the preparation of said compounds.

The present invention also comprises a pharmaceutical composition comprising the compounds of formula I, II or III and a pharmaceutically acceptable carrier; a method of treating a patient for diseases of schizophrenia, anxiety, variant angina, anorexia nervosa, Raynaud's phenomenon, intermittent claudication, coronary or peripheral vasospasms, fibromyalgia, cardiac arrhythmias, thrombotic illness and in controlling the extrapyramidal symptoms associated with neuroleptic therapy, depressive and bipolar disorders, obsessive-compulsive disorders, insomnia and sleep apnea, by administering a compound of formula I, II or III. Further, the present invention also comprises an intermediate, and methods of making the unsulfated versions of the forgoing compounds. The present invention also comprises collecting (isolating) the compounds of interest from a sample collected from a patient.

DETAILED DESCRIPTION OF THE PRESENT INVENTION (1) "Pharmaceutically acceptable salt" means either an acid addition salt or a basic addition salt, which is compatible with treatment of patients for the intended use.

"Pharmaceutically acceptable acid addition salt" is a non-toxic organic acid addition salt of the base compounds represented by Formula I, II or III or any of its intermediates. Some examples of inorganic acids which form suitable salts include hydrochloric, hydrobroinic, sulfixic and phosphoric acid and acid metal salts such as sodium monohydrogen orthophosphate, and potassium hydrogen sulfate. Illustrative organic acids, which form suitable salts, include the mono-, di, and tricarboxylic acids. Examples of such acids are acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as methane sulfonic acid, p-toluenesulfonic acid, and 2-hydroxyethane sulfonic acid. Such salts can exist in either a hydrated or substantially anhydrous form. In general, the acid addition hydrophilic organic salts in comparison to their free base forms generally demonstrate higher melting points.

"Pharmaceutically acceptable base addition salts" means non-toxic organic or inorganic basic addition salts of the compounds of Formula (I) or any of its intermediates. Examples are alkali metal or alkaline-earth metal hydroxides such as sodium, potassium, calcium or organic amines such as methylamine, trimethylamine and picoline.

(2) "Patient" means a warm blooded animal, such as, for example, rat, mouse, dog, cat, guinea pig, and primates such as a human.

(3) "Treat" or "treatment" means to prevent or alleviate symptoms, eliminate the causation of the symptoms either on a temporary basis, or to prevent or slow the appearance of symptoms of the named disorder or condition.

(4) "Therapeutically sufficient amount" means a quantity of the compound that is effective in treating the named disorder or condition.

(5) "Amount sufficient to antagonize the effects of serotonin at the 5 $HT_{2A}$ receptor" means a quantity of the compound that is effective in antagonizing the effects of serotonin at the $5HT_{2A}$ receptor.

(6) "Administering or administration" means a suitable route for giving a therapeutically sufficient amount of drug to a patient. Examples of suitable routes are oral, buccal, sublingual, parenteral, intravenous and topical, including a topical patch administration. Furthermore, this also means giving a prodrug to the patient in order to produce the compound of interest at the site of action in the body. For example, the prodrug (+)-α-(2,3-dimethoxyphenyl)-1-[2-(4-fluorophenyl)ethyl]-4-piperidinemethanol is administered to the patient to provide at least the compound sulfuric acid mono-(+)-[3-({1-[2-(4-fluoro-phenyl)-ethyl]-piperidin-4-yl}-hydroxy-methyl)-2-methoxy-phenyl]ester and possibly the (−) enantiomer thereof.

(7) "Schizophrenia" means a condition where a patient suffers a mental disturbance that lasts at least 6 months and includes 1 month of active-phase symptoms, such as two or more of the following: delusions, hallucinations, disorganized speech, grossly disorganized or catatonic behavior, and negative symptoms.

(8) "Anxiety" means a condition where a patient suffers an apprehension of danger and dread accompanied by restlessness, tension, tachycardia and dyspnea unattached to a clearly identifiable stimulus.

(9) "Variant angina" means a condition where the patient suffers from coronary vasospasms, which produce the chest pains associated with angina. These vasospasms typically occur while the patient is at rest.

(10) "Anorexia nervosa" means a condition where a patient refuses to maintain a minimally normal body weight and is intensely afraid of gaining weight, and exhibits a significant disturbance in the perception of the shape or size of his or her body.

(11) "Raynaud's phenomenon" means a condition where the patient suffers from a spasm of the digital arteries, with blanching and numbness of or pain of the fingers, often precipitated by cold.

(12) "Intermittent claudication" means a condition where the patient suffers from, due to ischemia of the muscles, attacks of lameness and pain, brought on by walking, chiefly in the calf muscles; however, the condition may occur in other muscle groups.

(13) "Coronary or peripheral vasospasms" means a condition where the patient suffers from contraction and hypertonia of the muscular coats of the cardiac or peripheral blood vessels.

(12) "Fibromyalgia" means a condition where the patient suffers chronically from numerous symptoms such as, for example, widespread generalized musculoskeletal pains, aching, fatigue, morning stiffness and a sleep disturbance which can be characterized as an inadequacy of stage 4 sleep.

(13) "Cardiac arrhythmia" means a condition where a patient suffers from any variation from the normal rhythm of the heart beat.

(14) "Thrombotic illness" means a condition where the patient suffers from a clotting within a blood vessel, which may cause infarction of tissues supplied by the vessel.

(15) "Extrapyramidal symptoms" means a condition where the patient suffers from side effects from the administration of neuroleptic agents such as haloperidol and chloropromazine. These extrapyramidal side effects (EPS) can encompass Parkinsonian-like syndromes, akathasia and acute dystonic reactions.

(16) "Depression" means a condition where the patient suffers from a temporary mental state or chronic mental disorder characterized by feelings of sadness, loneliness, despair, low self-esteem and self-reproach; accompanying signs include psychomotor retardation or less frequently agitation, withdrawal from social contact and vegetative states such as loss of appetite and insomnia.

(17) "Bipolar disorder" means a condition where the patient suffers from alternating periods of euphoria and depression.

(18) "Obsessive-compulsive disorders" or "OCD" means a condition where the patient exhibits recurrent obsessions or compulsions that are severe enough to be time consuming (i.e., take more than an hour a day) or cause marked distress or significant impairment. Obsessions are persistent ideas, thoughts, impulses, or images that are experienced as intrusive and inappropriate and that cause marked anxiety or distress. Compulsions are repetitive behaviors (e.g., hand washing, ordering, checking) or mental acts (e.g., praying, counting, repeating words silently) the goal of which is to prevent or reduce anxiety or distress, not to provide pleasure or gratification.

(19) "Insomnia" means a condition where the patient suffers from an inability to sleep in the absence of external impediments, during the period when sleep should normally occur.

(20) "Sleep apnea" means a condition where the patient suffers from a stoppage of breathing for at least 10 seconds or more, and usually greater than 20 times/hour, causing measurable blood deoxygenation.

(21) "Pharmaceutically acceptable carrier" is a non-toxic solvent, dispersant, excipient, adjuvant or other material, which is mixed with the active ingredient in order to permit the formation of a pharmaceutical composition, i.e., a dosage form capable of administration to the patient. One example of such a carrier is pharmaceutically acceptable oil typically used for parenteral administration.

(22) "Enantiomers" are a pair of isomers that are mirror images of each other and not superposable.

(23) "Racemate" means a composite of two enantiomeric species. It is devoid of optical activity.

(24) "Stereoisomer" is a general term for all isomers of individual molecules that differ only in the orientation of their atoms in space. It includes mirror image isomers (enantiomers), geometric (cis/trans) isomers and isomers of compounds with more than one chiral center that are not mirror images of one another (diastereomers).

(25) "$C_1$–$C_4$ alkyl" and $C_{1-6}$ alkyl" means a straight or branched chain hydrocarbon radical of one to four and one to six carbon atoms. Included within the scope of these terms are methyl, ethyl, n-propyl, isopropyl, n-butyl, isobutyl, pentyl, neopentyl, hexyl and the like.

(26) "Aralkyl" means an aryl or diaryl moiety connected to the remainder of the molecule via an alkylene bridge. This alkylene bridge can be straight or branched-chained and is one, two, three, four, five or six carbons in length. "Aryl" means an aromatic radical having six atoms in a single ring system such as phenyl or a fused ring system such as 1-napthyl, 2-napthyl and the like. The aryl or diaryl group may be optionally substituted as described herein. The substitutions may be at the ortho, meta or para positions as appropriate. Examples of preferred aralkyls are benzyl, phenylethyl, propylphenyl and diphenylbutyl.

(27) "Optionally substituted" means that the referenced moiety is substituted as defined herein by the same or different substituents, i.e. independently selected, from the group; of hydrogen, halogen (fluorine, chlorine, iodine or bromine), $C_{1-6}$ alkyl, $C_{1-6}$ alkoxy, C(=O)H, C(=O) $C_{1-6}$ alkyl, $CF_3$ or hydroxy with one, two or three substituents as is suitable to the structure.

(28) "Prodrug" means a compound given to a patient, which is then metabolized in the patient to another active compound. In the present invention the prodrug is (+)-α-(2, 3-dimethoxyphenyl)-1-[2-(4-fluorophenyl)ethyl]-4-piperidinemethanol.

(29) "Sample" means a quantity of either plasma, urine or other component of the body from which the compounds of the present invention may be found and isolated therefrom.

(30) "Optically active isomers" are isomers that rotate the plane of polarized light and are designated (+) or (−).

The compounds of the invention may be prepared by the synthetic routes described below in the Schemes or other methods, which may be apparent to those skilled in the art. The enantiomerically pure compounds of the invention may be prepared as outlined in Scheme A. The scheme illustrates the synthesis of the (+) enantiomer; however, as would be evident to one with ordinary skill in the art, by starting with the appropriate (−) enantiomer the sequence shown in Scheme A would afford the corresponding (−) enantiomer of the invention.

Scheme A

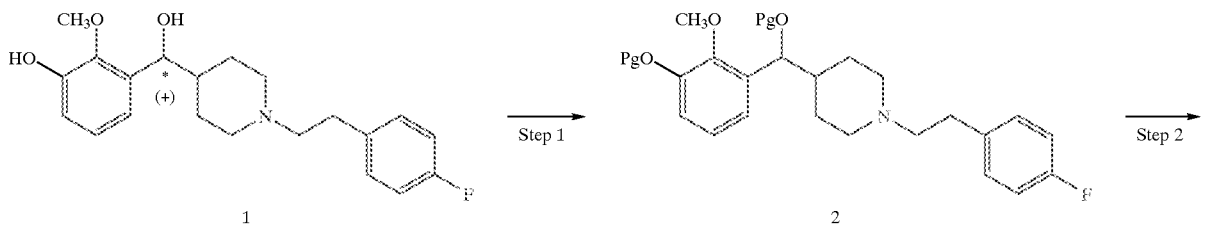

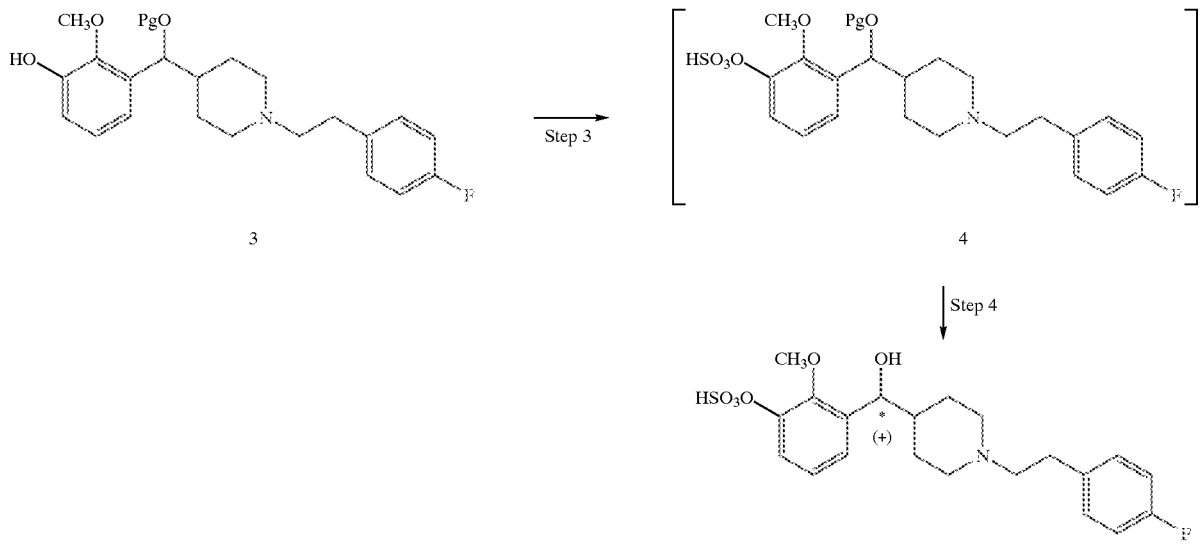

Formula II
(Compound of Formula III is formed from (-) isomer of 1)

Step A1: The compound 1, (+)-α-(3-hydroxy-2-methoxyphenyl)-1-[2-(4-fluorophenyl)ethyl]-4-piperidinemethanol, a known metabolite of (+)-α-(2,3-dimethoxyphenyl)-1-[2-(4-fluorophenyl)ethyl]-4-piperidinemethanol as described in Heath, F. G. et al. *J. Am. Soc. Mass Spectrom.* (1997), 8(4), 371–379, and Scott, D. et al. *J. Pharm. Biomed. Anal.* (1998), 17(1), 17–25, (also see Scheme C), is reacted with a suitable acylating agent to provide the diprotected compound 2, wherein Pg is a protecting group such as $C_{1-6}$ alkylsulfonyl, trifluoroacetyl, or $C(=O)$ $C_{1-6}$ alkyl other protecting groups may be used as is known to one skilled in the art. The groups may be the same or different groups, but typically are the same. Suitable acylating agents are, for example, anhydrides and acid chlorides or bromides, with anhydrides preferred. The reaction is performed under standard acylating conditions well known to those with ordinary skill in the art.

Step A2: The diprotected compound 2 is then selectively hydrolyzed to the monoprotected phenol 3. The reaction may be carried out in an aqueous protic solvent with an alkali bicarbonate. Examples of aqueous protic solvents are ethanol, methanol, propanol and isopropanol that have been diluted with varying proportions of water. The preferred aqueous protic solvent is aqueous methanol. Examples of alkali bicarbonates are sodium, cesium or potassium bicarbonate, sodium bicarbonate being preferred. The reaction temperature may vary from 0° C. to the boiling point of the solvent. The preferred temperature is between 0° C. and room temperature.

Step A3: The monoprotected phenol 3 is converted to the intermediate mono sulfuric acid ester 4 by reacting said monoprotected phenol with a suitable sulfating agent. Suitable sulfating agents are those compounds capable of adding sulfate at the desired position. Examples of suitable sulfating agents are sulfur trioxide pyridine complex, sulfur trioxide triethylamine complex, sulfur trioxide dimethylformamide complex, sulfuric acid-dicyclohexylcarbodiimide, chlorosulfonic acid with acid or base. pyridine sulfur trioxide complex being preferred. The reaction is carried out in an appropriate organic solvent. Examples of appropriate organic solvents are benzene, toluene, acetonitrile, dimethylformamide, dichloromethane and chloroform. The preferred solvent is acetonitrile. The reaction temperature may vary from room temperature to the boiling point of the solvent, a temperature of about 45° C. is preferred.

Step A4: Preferably without isolation of the sulfuric acid ester 4 is reacted in situ with an alkali metal carbonate such as sodium, potassium, or cesium carbonate, potassium carbonate preferred, in an aqueous protic solvent such as methanol-water to afford the sulfuric acid ester alcohol 5. The reaction temperature may vary from room temperature to boiling point of the solvent, the boiling point of the solvent is preferred.

Scheme B illustrates the synthesis of the racemate of 15 also known as Formula I.

Scheme B

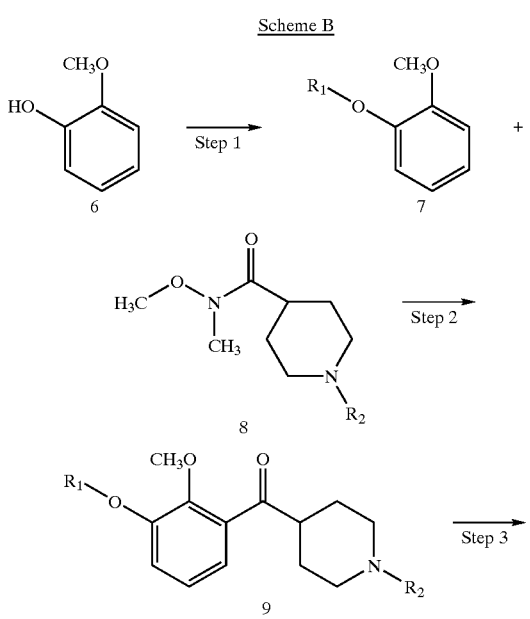

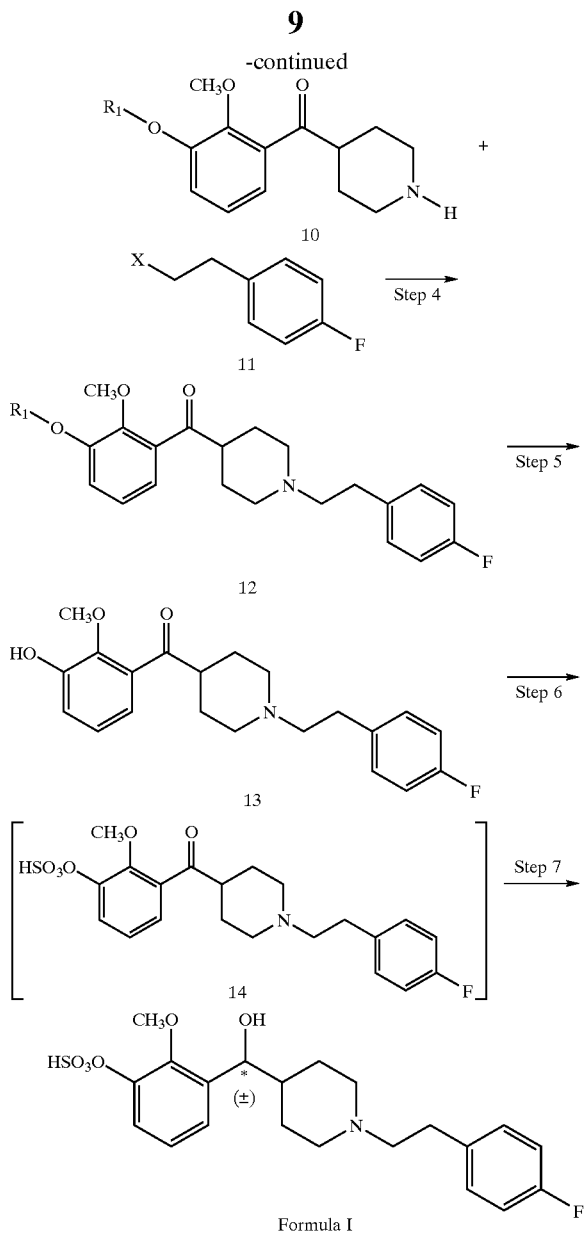

Step 1: Guiacol, the compound 6, available from the Aldrich Chemical Company, is reacted with a reagent to provide a suitable protecting group, preferably a suitable trialkylsilyl halide to form the monomethoxysilylether derivative 7. Suitable trialkylsilyl halides are compounds that would react with a phenolic oxygen to produce a compound wherein $R_1=Si(R_4)_3$ and $R_4$ is $C_{1-6}$ alkyl, for example, t-butyldimethylsilyl chloride and triisopropylsilyl chloride, with triisopropylsilyl chloride being preferred. The purpose of the silyl substituent ($R_1$), besides protecting the phenolic oxygen, is also to inhibit abstraction of the aromatic hydrogen that is adjacent (ortho) to the $OR_1$ substituent, when the compound is treated with a strong base. Consequently, upon reaction of said compound with a strong base, the aromatic hydrogen ortho to the methoxy substituent is abstracted regioselectively. Such a strategy has been previously invoked by B. Trost, et al., *Tetrahedron Lett.*, 1985, 26, 123–126 and J. J. Landi, et al. *Synthetic Commun.*, 1991, 21, 167–171 incorporated herein by reference. The reaction is typically effected by reaction of a trialkylsilyl halide, in the presence of a suitable nucleophilic catalyst such as imidazole or 4-dimethylaminopyridine, imidazole being preferred, in a suitable polar aprotic solvent. Examples of polar aprotic solvents are dimethylformamide, 1-methyl-2-pyrrolidinone, dimethylsulfoxide, hexamethylphosphor-amide, acetone and acetonitrile. The preferred solvent is dimethylformamide. The reaction can be run at a temperature from 0° C. to ambient temperature, ambient temperature being preferred.

Step: B2: The silyl derivative 7 is then reacted with a $C_{1-4}$ alkyl lithium, such as n-butyl, sec-butyl or t-butyl lithium, n-butyl lithium being preferred, in an ethereal solvent, such as diethyl ether, tetrahydrofuran or dimethoxyethane, with tetrahydrofuiran being the preferred solvent. This results in the regioselective formation of the anion. Addition of a suitable N-protected piperidinyl Weinreb amide derivative 8, produces the ketone 9. Suitable N-protecting groups ($R_2$) are those that would be stable under the reaction conditions, and examples can be found in *Protective Groups in Organic Synthesis*, 2nd edition, Theodora Greene, et al., John Wiley and Sons, Inc., incorporated herein by reference. The reaction temperature may be varied between −78° C. to the boiling point of the solvent.

Step B3: The ketone 9 is N-deprotected to produce the aroyl piperidine10. Reagents and conditions to effect the deprotection would depend upon the nature of the N-substituent and would be apparent to one with ordinary skill in the art.

Step B4: Reaction of aroyl piperidine 10 with a suitable alkylating agent 11 forms the alkylated piperidine 12. A suitable alkylating agent is where X=a suitable leaving group. A "suitable leaving group" is a moiety that is displaced or removed for the reaction to take place. Examples of suitable leaving groups are halogens, benzenesulfonate, methanesulfonate or p-toluenesulfonate, with methanesulfonate being preferred. The reaction is performed in the presence of a suitable organic base, in a polar aprotic solvent. Examples of suitable organic bases are pyridine, triethylamine. lutidine and N-ethyldiisopropylamine, with N-ethyldi-isopropylamine preferred. Examples of suitable polar aprotic solvents are acetone, acetonitrile, dimethyl formamide, 1-methyl-2-pyrrolidinone, dimethylsulfoxide and hexamethylphosphoramide. The preferred solvent is acetonitrile. The reaction may be conducted at room temperature to the boiling point of the solvent. The preferred temperature being the boiling point of the solvent.

Step B5: The alkylated piperidine 12 is converted to the hydroxy ketone 13 by treatment with a suitable desilylating agent in an ethereal solvent. A suitable desilylating agent is a compound, which removes the silyl protecting group. Examples of suitable desilylating agents are ammonium tetrafluoride, tetra-N-butylammonium fluoride and pyridine hydrofluoride, tetra-N-butylammonium fluoride being preferred. Suitable ethereal solvents are diethyl ether, tetrahydrofuran or dimethoxyethane, tetrahydrofuran being preferred. The reaction temperature may vary from 0° C. to the boiling point of the solvent, with ambient temperature being preferred.

Step B6: Hydroxy ketone 13 is converted to the intermediate sulfuric acid ester 14 by reacting said hydroxyketone with a suitable sulfating agent. Suitable sulfating agents are those compounds capable of adding sulfate at the desired position. Examples are sulfur trioxide pyridine complex, sulfur trioxide triethylamine complex, sulfur trioxide dimethylformamide complex, sulfuric acid-dicyclohexylcarbodiimide and chlorosulfonic acid with acid or base. The reagent sulfur trioxide pyridine complex being preferred. The reaction is carried out in an appropriate organic solvent for the reaction to occur. Examples of appropriate organic solvents are benzene. toluene. acetonitrile, dimethylformamide, dichloromethane and chloroform. The preferred solvent is acetonitrile. The reaction temperature may vary from room temperature to boiling point of the solvent. The preferred temperature being the boiling point of the solvent.

Step B7: Preferably without isolation, the sulfuric acid ester ketonel4 is reduced to the racemic alcohol ester 15, by an suitable reducing agent. A suitable reducing agent is a compound, which reduces this ketone to the desired alcohol. Examples of suitable reducing agents are alkali metal borohydrides, such as lithium or sodium borohydride with sodium borohydride being the preferred reducing agent. The reaction is performed in an appropriate protic organic solvent such as ethanol, isopropanol, propanol or methanol, ethanol being the preferred solvent. The reaction temperature may vary from 0° C. to the boiling point of the solvent, with room temperature being preferred.

Step B8: Optionally reacting compound 15 or its enantiomers with an inorganic or organic acid capable of forming a pharmaceutically acceptable salt.

In another embodiment of this invention, the method of synthesis of the intermediate alcohol 1 is described in Scheme C.

and aliphatic ethers such as diethyl and diisopropyl ether. The preferred solvent being toluene. Suitable bases would be tertiary organic amines, and aqueous solutions of inorganic bases. Inorganic bases suitable for use in the present invention include alkali hydroxides, alkali carbonates and alkali bicarbonates. Most preferred is an aqueous solution of an alkali hydroxide such as sodium hydroxide.

Step C2: The ketoamide 17 is reduced to produce the piperidine alcohol 18 as a racemate with a suitable reducing agent in an organic solvent. Reducing agents suitable for use in the method are borane complexes, aluminum hydrides, alkali aluminum hydrides, alkali borohydrides particularly in the presence of Lewis or organic acids. The preferred reducing agent is borane-methyl sulfide complex. Organic solvents that can typically be used for the reaction are ether, tetrahydrofuran, dimethoxyethane and toluene, with toluene being preferred. The reaction temperature at which the reaction can be run may vary from −50° C. to the boiling point of the solvent. Most preferred is a temperature of about −30° C. to room temperature.

In a further embodiment, the piperidine alcohol 18 can be obtained in an enantioenriched state by the addition of a catalytic amount of a chiral oxazaborolidine to Step C2 above. The use of such reagents for the enantioselective reduction of ketones has been illustrated in a review by

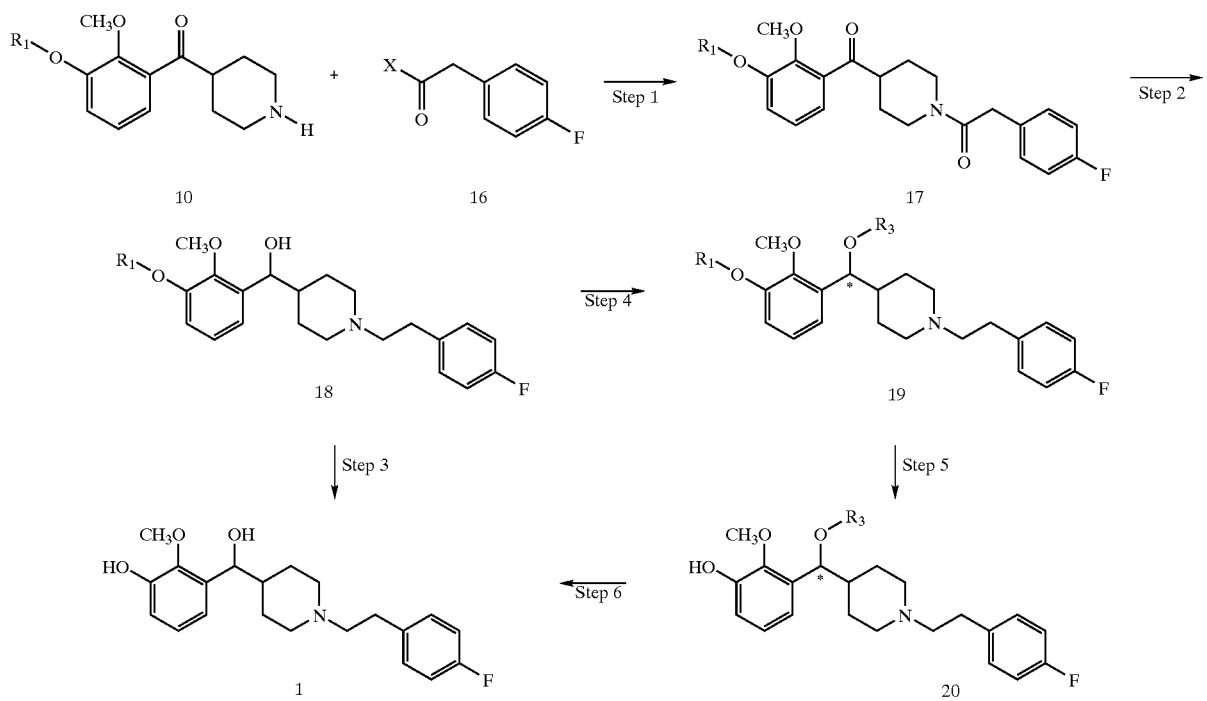

Scheme C

Step C1: The benzoyl piperidine 10 from Scheme B is reacted with the acid halide 16 to obtain the ketoamide 17. The substituent X represents a halogen chosen from Br, Cl and F with Cl being the preferred halogen. The substituent $R_1$ represents the group $Si(R_3)_4$ and $R_3$ represents $C_{1-4}$ alkyl. The reaction can be performed under conditions that are well known to one skilled in the art, for instance, in a suitable organic solvent and in the presence of a suitable base. Examples of suitable organic solvents are aromatic hydrocarbons such as benzene, toluene, mesitylene and xylenes; aliphatic hydrocarbons such as pentane. hexane and heptane Walbine S. et al., Tetrahedron Assymetry. 1992, 3, 1475–1504, incorporated herein by reference. Suitable chiral oxazaborolidines for the reaction are (R) or (S)-3,3-diphenyl1-substituted pyrrolidino[1,2-c]-1,3,2-oxazaboroles and (R) or (S)-3,3-di-β-naphthyl1-substituted pyrrolidino[1,2-c]-1,3,2-oxazaboroles. The preferred chiral catalyst being (R) or (S)-3,3-diphenyl-1-methylpyrrolidino[1,2-c]-1,3,2-oxazaborole (2-methyl-CBS-oxazaborolidine or methyl oxazaborolidine).

Step C3: Optionally, the piperidine alcohol 18 can be deprotected to produce the racemate of the phenol alcohol I by treatment with a suitable desilylating agent in an organic solvent. A suitable desilylating agent is a compound, which removes the silyl protecting group. Examples of suitable desilylating agents are ammonium tetrafluoride, tetra-N-butylammonium fluoride and pyridine hydrofluoride, with ammonium tetrafluoride preferred. Suitable organic solvents for the reaction are protic solvents such as alcohols or ethereal solvents such as dialkyethers. The reaction temperature may vary from ambient temperature to the boiling point of the solvent.

Step C4: The piperidine alcohol 18 as a racemate or in enantioenriched form can then be reacted with a suitable chiral acid to give a mixture of diastereomeric esters 19, wherein $R_3$ is a suitable resolving agent. Suitable resolving agent means a moiety capable of separating enantiomers from a racemate by formation of diastereomeric esters. Some examples of suitable resolving agents are (R) or (S) mandelic acid, acetyl mandelic acid, α-methoxyphenylacetic acid, α-methoxy-α-(trifluoromethyl)-phenylacetic acid, -2-(6-methoxy-2-naphthyl)-propionic acid, ω-camphanic acid, trans-1,2-cyclohexane dicarboxylic acid anhydride and 5-oxo-2-tetrahydrofurancarboxylic acid as described in *Stereochemistry of Organic Compounds,* Ernest L. Eliel et al., John Wiley & Sons. Inc., incorporated herein by reference. The preferred resolving agent is (R) or (S) α-methoxyphenylacetic acid. The reaction is typically performed in an organic solvent in the presence of a coupling promoter such as dicyclohexylcarbodiimide or carbonyl diimidazole and a nucleophilic catalyst such as imidazole or 4-dimethylamino-pyridine. The preferred coupling promoter is dicyclohexylcarbodiimide, and the preferred nucleophilic catalyst is 4-dimethylaminopyridine. Suitable organic solvents for the reaction are aprotic solvents such as chloroform, methylene chloride, dimethylformamide, acetonitrile and toluene, with methylene chloride being preferred. The reaction may be performed at room temperature to the boiling point of the solvent, the boiling point of the solvent is the preferred temperature. The mixture of diastereomeric esters is then separated by techniques that are well known to one with ordinary skill in the art, to produce the two individual diastereomers of compound 19. Separation of the diastereomers, for example, can be accomplished by crystallization or column chromatography, with the preferred method of separation being chromatography.

Step C5: The pure individual diastereomer of 19 is converted to the phenol ester 20 by treatment with a suitable desilylating agent in a protic solvent. Examples of suitable desilylating agents are ammonium tetrafluoride tetra-N-butylammonium fluoride and pyridine hydrofluoride, with ammonium tetrafluoride preferred. Suitable protic solvents are methanol, ethanol, propanol, butanol and isopropanol, methanol being preferred. The reaction temperature may vary from ambient temperature to the boiling point of the solvent, the boiling point of the solvent being preferred.

Step C6: The phenol ester 20 is hydrolyzed to a single enantiomer of the phenol alcohol 1 by reaction of the ester with a suitable base in a water-protic solvent solution. Suitable bases to effect the reaction are alkali metal hydroxides and carbonates, such as sodium, potassium, lithium and cesium hydroxides and carbonates. with the preferred base for the reaction being potassium carbonate. Suitable water-protic solvent solutions are methanol-water, ethanol-water, propanol-water, isopropanol-water and butanol-water, with methanol-water preferred. The reaction temperature may vary from 0° C. to the boiling point of the solvent, with a temperature of about 20–25° C. preferred.

Also, as a further embodiment of the invention compound 1 can be isolated as an acid addition salt, whose preparation can be accomplished by methods that are well known to one with ordinary skill in the art.

The compounds of the current invention may be isolated from a sample such as human plasma by taking a sample of said human plasma from a patient that has been administered a therapeutically effective amount of (+)-α-(2,3-dimethoxyphenyl)1-[2-(4-fluorophenyl)ethyl]-4-piperidinemethanol, treating the sample by methods well-known to one with ordinary skill in the art, and subjecting said sample to isolation techniques such as chromatography. Chromatography of the sample can be accomplished, for example, by such techniques as high performance liquid chromatography, column chromatography, thin layer chromatography and gas chromatography. The most preferred method of isolation is high performance liquid chromatography.

The stereochemistry of the isolated compound will be dependent upon the metabolic process, and thus may be isolated from the patient as a racemate or a single enantiomer.

The dosage range at which sulfuric acid mono -[3-({1-[2-(4-fluoro-phenyl) ethyl]-piperidin-4-yl}-hydroxy-methyl)-2-methoxy-phenyl]ester and its enantiomers exhibit their ability to block the effects of serotonin at the $5TH_{2A}$ receptor can vary depending upon the particular disease or condition being treated and its severity, the patient, other underlying disease states the patient is suffering from, and other medications that may be concurrently administered to the patient. Generally though, the compounds will exhibit their serotonin $5TH_{2A}$ antagonist properties at a dosage range of from about 0.001 mg/kg of patient body weight/day to about 100.0 mg/kg of patient body weight/day. These compounds are typically administered from 1–4 times daily. Alternatively, they can be administered by continuous infusion. The compounds can be administered orally or parenterally to achieve these effects.

The compound of the present invention intended for administration can be formulated into pharmaceutical dosage forms using techniques well known in the art. For oral administration, the compound can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compound can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

For parenteral administration, the compound or its salts may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc. as are known in the art.

The compound may be admixed with any inert carrier and utilized in laboratory assays in order to determine the concentration of the compounds within the urine, serum, etc. of the patient as is known in the art.

The following examples present typical syntheses as described by Schemes A, B and C and methods for isolation and biological assays. These examples are understood to be illustrative only and are not intended to limit the scope of the invention in any way. As used in the following examples, the following terms have the meanings indicated: "g" refers to grams, "mg" refers to milligrams "mmol" refers to millimoles, mol refers to moles, "mL" refers to milliliters, "μL" refers to microliters "μm" refers to micromoles, " "μM" refers to micromolar, "mM" refers to millimolar "ppm" refers to parts per million, "C" refers to Celsius, "THF" refers to tetrahydrofuran. "MeOH" refers to methanol, "EtOAc" refers to ethyl acetate, "TLC" refers to thin layer chromatography, "LC" or "HPLC" refers to high performance liquid chromatography and "CIMS" refers to chemical ionization mass spectrum, "CIDMS" refers to collision-induced dissociation mass spectrum. "NMR" refers to nuclear magnetic resonance, "IR" refers to infrared spectroscopy "$t_R$" means retention time, "$R_f$" means the ratio of the distances which the sample migrates (on TI,C) as compared to the distance from the starting point of the solvent front.

EXAMPLE 1A

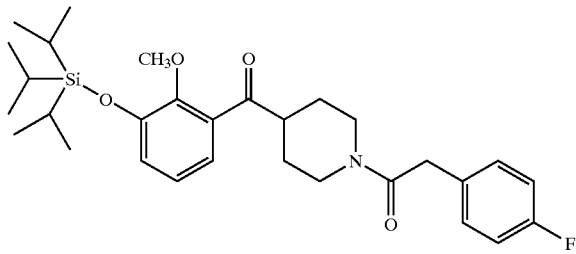

2-(4-Fluoro-phenyl)-1-[4-(2-methoxy-3-triisopropylsilanyloxy-benzoyl)-piperidin-1-yl]-ethanone To a solution of 4-(2-methoxy-3-triisopropylsilanyloxy-benzoyl)-piperidine of Example 2C below (287 g, 0.72 mol) in toluene (750 mL) add 50% NaOH (102 mL) and H₂((300 mL). Cool the mixture in an ice bath and add 4-fluorophenacetyl chloride (221.3 g, 1.28 mol) dissolved in toluene over a period of 30 min. Allow the reaction to warm to room temperature, and stir for 2 h. Add H₂O (500 mL), stir for 0.5 h and separate the phases. Dry the organic layer (MgSO₄) and concentrate to obtain 482 g of a brown oil. Purify the oil by flash chromatography over silica gel in three separate portions, eluting with ethyl acetate/hexanes. Combine like fractions to obtain two batches of oil: 123 g and 269 g. Treat the smaller batch with 1:9 ethyl acetate/hexane and filter away 28 g of 4-flurorophenyl acetic acid. Concentrate the filtrate to obtain 95 g of oil, combine with the larger batch and dissolve in 1:1 ethyl acetate/hexane (1.5 L). Wash the organic solution with 4% NaOH (1 L), 2% NaOH (1 L), 2% HCl (1 L), saturated NaHCO₃ (1 L) and H₂O(1 L). Dry the organic layer (MgSO₄), filter and concentrate to obtain 270 g of the title compound.

EXAMPLE 1B

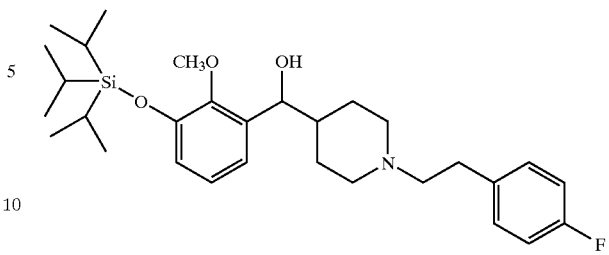

{1-[2-(4-Fluoro-phenyl)-ethyl]-piperidin-4-yl}-(2-methoxy-3-triisopropylsilanyloxy-phenyl)-methanol To a solution of 2-(4-Fluoro-phenyl)-1-[4-(2-methoxy-3-triisopropylsilanyloxy-benzoyl)-piperidin-1-yl]-ethanone, Example 1A (262 g, 0.496 mol) in toluene (3.8 L) at −38° C. add (R)-methyloxoazaborolidine (150 mL, 0.15 mol, of 1M solution in toluene), follow with the addition of borane dimethylsulfide complex (750 mL of a 2M solution in toluene, 1.5 mol), over a 2 h period at −30° C. Stir between −25° C. to -28° C. overnight and then allow the reaction to warm to ambient temperature over a 2 h period. Slowly add MeOH (500 mL) over a1 h period and then concentrate the solution to obtain 363 g of yellow oil. Add MeOH (1.8 L) to the oil and concentrate under reduced pressure at 80° C. to obtain 341 g of a yellow oil. Purify the oil by plug filtration through silica gel eluting with 1:1 MeOHI/CHCl₃. Combine and concentrate the desired fractions to obtain 250 g of product. Further purify the product by column chromatography over silica gel eluting with 1:3 EtOAc/hexane (20 L), 1:1 EtOAc/hexane (20 L) and 1:1 CHCl₃/MeOH (40 L). Collect and concentrate like fractions to obtain 214 g of oil. Dissolve the oil in CHCl₃ (500 mL)/toluene (600 mL), dry (MgSO₄) and concentrate to obtain 207 g of the title compound as a foam.

EXAMPLE 1C

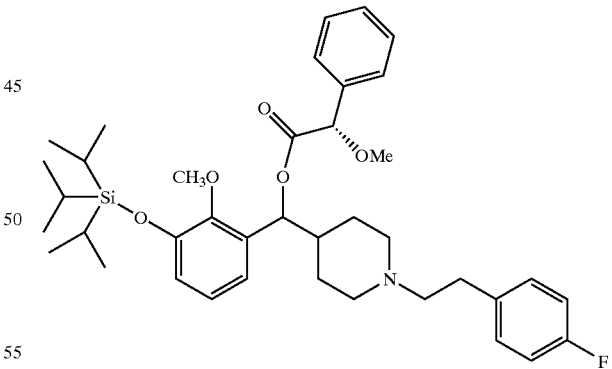

(S)-Methoxy-2-phenyl-acetic acid {1-[2-(4-fluoro-phenyl)-ethyl]-piperidin-4-yl}-(2-methoxy-3-triisopropylsilanyloxy-phenyl)-methyl ester Stir a solution of {1-[2-(4-fluoro-phenyl)-ethyl]-piperidin-4-yl}-(2-methoxy-3-triisopropylsilanyloxy-phenyl)-methanol, Example 1B (233.5 g, 0.53 mol) in CHCl₃ (2 L), add (S)-(+)-α-methoxyphenyl acetic acid (91 g, 0.55 mol) in CH₂Cl₂ (40 mL) 1,3dicyclohexylcarbodiimide (11.2 g, 0.54 mol) and 4-dimethylaminopyridine (0.3 g, 0.008 mol). Heat the reaction to reflux for 17 h, cool in an ice bath and add hexane (1 L). Filter the mixture to remove the by-product urea and concentrate to obtain 368 g of yellow oil. Add hexane (1.4 L) to the oil and heat to dissolve. Cool the solution to ambient temperature and allow standing for 24 h. Filter off more urea and concentrate the filtrate with 630 g of silica gel. Apply the coated silica gel to a column previously packed with silica gel and elute with 1:5 EtOAc/hexane (80 L) and 1:2 EtOAc/hexane (20 L). Concentrate like fractions and obtain a semi-solid. Treat the semi-solid with hexane and filter away the last traces of the urea. Concentrate the filtrate to obtain 207.2 g of yellow oil.

EXAMPLE 1D

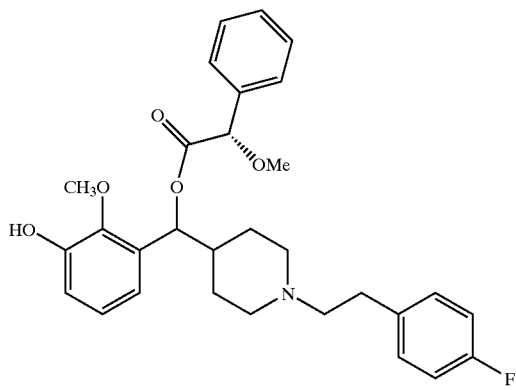

(S)-Methoxy-2-phenyl-acetic acid {1-[2-(4-fluoro-phenyl)-ethyl]-piperidin4-yl}-(3-hydroxy-2-methoxy-phenyl)-methyl ester Add to methoxy-phenyl-acetic acid {1-[2-(4-fluoro-phenyl)-ethyl]-piperidin-4-yl}-(2-methoxy-3-triisopropylsilanyloxy-phenyl)-methyl ester, Example 1C (207 g, 0.3111 mol) a 0.5M solution of methanolic ammonium tetrafluoride (1.2 L, 0.6 mol) and reflux for 17.5 h. Concentrate and obtain 198 g of the title compound.

EXAMPLE 1E

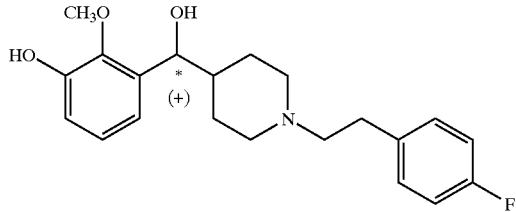

(+)1-[2-(4-Fluorophenyl-)ethyl]-α-(3-hydroxy-2-methoxyphenyl)-piperidinemethanol Add to a solution of methoxy-phenyl-acetic acid {1-[2-(4-fluoro-phenyl)-ethyl]-piperidin-4-yl}-(3-hydroxy-2-methoxy-phenyl)-methyl ester, Example 1D (158.2 g, 0.311 mol) in MeOH (1.2 L), $K_2CO_3$ (96.2 g, 0.676 mol). Stir the reaction mixture at ambient temperature for 16 h add $H_2O$ (163 mL) and continue to stir for 16.5 h. Cool the reaction to ambient temperature and concentrate. Stir the residue in $CHCl_3$ (1.5 L)-$H_2O$ (1 L) for 10 min and separate the organic layer. Wash the organic phase with $H_2$ (500 mL), dry ($MgSO_4$) and concentrate to 140 g of white foam. Purify the product by flash chromatography over silica gel eluting with 1.5:1 $CHCl_3$/MeOH (40 L) and $CHCl_3$/MeOH (20 L). Combine and concentrate like fractions and dissolve the residue in EtOAc (1 L). Dry the solution ($MgSO_4$) and concentrate to obtain 86 g of the product as a white foam. $[\alpha]_D$(c=1.0, in methanol)=+25.3°.

EXAMPLE 1F

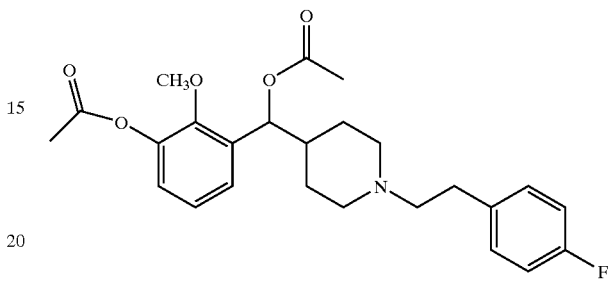

Acetic acid-(3-acetoxy-2-methoxy-phenyl)-{1-[2-(4-fluoro-phenyl)-ethyl]-piperidin-4-yl}-methyl ester Add acetic anhydride (5 mL), dropwise, over 10 min to a stirring, cooled (ice/water bath) solution of (+)-1-[2-(4-fluorophenyl-)ethyl]-α-(3-hydroxy-2-methoxyphenyl)-piperidinemethanol, Example 1E (4.0 g, 11.1 mmol) in pyridine (40 mL). Stir the reaction mixture overnight, while allowing the temperature to rise to ambient temperature. Add dichloromethane (100 mL) and wash the organics twice with aqueous bicarbonate solution (100 mL). Dry the organic layer over $Na_2SO_4$, filter and evaporate under vacuum and obtain 5.2 g of product.

EXAMPLE 1G

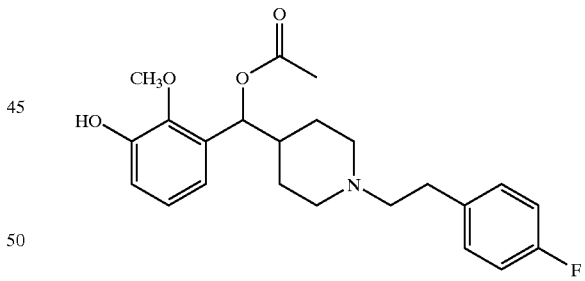

Acetic acid -{1-[2-(4-fluoro-phenyl)-ethyl]-piperidin-4-yl}-(3-hydroxy-2-methoxy-phenyl)-methyl ester Stir overnight a mixture of the acetic acid -(3-acetoxy-2-methoxy-phenyl)-{1-[2-(4-fluoro-phenyl)-ethyl]-piperidin-4-yl}-methyl ester, Example 1F (5.2 g, 1.1 mmol), $NaHCO_3$ (11 g, 130 mmol), methanol (100 mL) and water (50 mL). Add water (100 mL) and dichloromethane (100 mL), and separate the layers. Extract the aqueous layer with dichloromethane (100 mL), and combine the organic layers. Dry over $Na_2SO_4$ and filter. Remove the solvent under vacuum and obtain 5.1 g of product.

EXAMPLE 1H

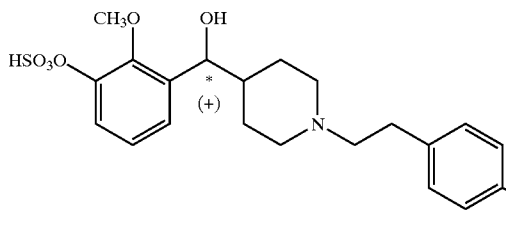

Sulfuric acid mono-(+)-[3-({1-[2-(4-fluoro-phenyl)-ethyl]-piperidin-4-yl}-hydroxy-methyl)-2-methoxy-phenyl]ester Add sulfur trioxide pyridine complex (10 g, 62 mmol) to a solution of the acetic acid-{1-[2-(4-fluoro-phenyl)-ethyl]-piperidin-4-yl}-(3-hydroxy-2-methoxy-phenyl)-methyl ester, Example 1G (5.1 g, 11.1 mmol) in acetonitrile (50 mL), and heat at 45° C. for 18 h. Cool the mixture to ambient temperature and add water (70 mL), methanol (70 mL) and $K_2CO_3$ (26 g. 0.194 mol). Reflux the mixture for 12 h. Evaporate the acetonitrile and methanol and acidify the remaining aqueous portion to pH=6. Collect the resulting precipitate, rinse with water and dry to obtain 3.0 g of a light, brown solid. The solid is 98% pure by LC (Zorbax Rx C8, 5 µ, 250×4.6 mm, 0.17M acetic acid-0.05M ammonium acetate buffer/acetonitrile, 75:25. Flow: 0.8 mL/min) $t_R$=9.40 min. CIMS, m/z=342 (M+H—$SO_3$—$H_2O$)$^+$. $^1$H NMR (300 MHz, DMSO-$d_6$)δ(ppm) 7.40 (d, 1H), 7.35 (t, 2H), 7.12 (t, 2H), 7.00 (d, 1H), 6.95 (d, 2H), 4.63 (t, 1H), 3.79 (s, 3H), 3.50–2.40 (series of broad peaks, 9H), 1.90–1.40 (series of broad peaks, 5H). $^{13}$C NMR (75 MHz, DMSO-$d_6$)δ=162.25, 159.95, 147.75, 145.59, 137.02, 130.05, 122.20, 121.5, 119.95, 115.05, 115.00, 69.03, 60.09, 57.00, 52.00, 33.33, 29.02, 26.02, 25.00, 24.05. $^{19}$F NMR (376 MHz, DMSO-$d_6$)δ=−117.00. [α]$_D$ (22° C., c=0.6033 in 2:1 DMSO/MeOH)=+28.9°.

EXAMPLE 2A

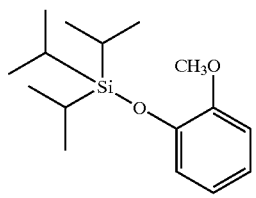

2-Methoxy-1-(triisopropylsilyloxy)benzene

To a solution, under nitrogen, of guiacol (1.0 g, 8.06 mmol) in DMF (20 mL) at ambient temperature add imidazole (1.15 g, 16.9 mmol) and triisopropylsilyl chloride (2,6 mL, 12.08 mmol). Allow reaction for 23.5 h and then pour into saturated $NaHCO_3$ solution (35 mL). Extract the aqueous mixture with hexane (3×50 mL), combine the extracts, wash with 1M HCl (50 mL), $H_2O$ (50 mL) and dry over $MgSO_4$. Filter through $Na_2SO_4$ and concentrate under vacuum. Distill the product with a Kugelrohr apparatus under high vacuum and collect 2.14 g of colorless oil.

anal. Calc. for $C_{16}H_{28}O_2Si$: C,68.50;H, 10.08. Found: C, 68,45;H, 9.92. CIMS ($CH_4$): m/z=281 (81%), 237 (100%). IR (KBr): 2945, 2868, 1504, 1458, 1267, 920, 745 cm$^{-1}$. $^1$H NMR (CDCl$_3$): δ6.90–6.75 (4 H), 3.79 (3 H, m), 1.09 (6 H, d, J=7.1 Hz). $^{13}$C NMR (CDCl$_3$): δ(ppm) 150.9, 145.5, 121.3, 120.7, 120.7, 120.5, 112.2, 55.4, 17.9, 12.9.

EXAMPLE 2B

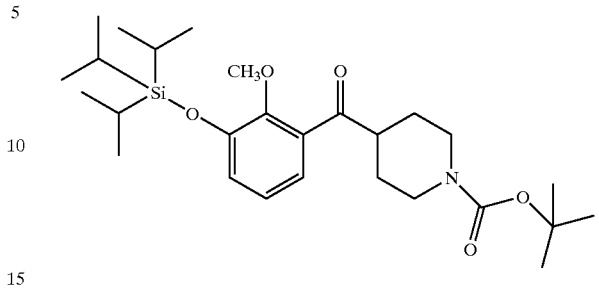

4-(2-Methoxy-3-triisopropylsilanyloxy-benzoyl)-piperidine-1-carboxylic acid tert-butyl ester Cool in a dry ice/acetone bath under nitrogen, a solution of 2-methoxy1-(triisopropylsilyloxy)benzene, Example 2A (0.560 g, 2.00 mmol) in dry THF (5.0 mL) and add 2.5M n-butyllithium in hexane (3.2 mL, 8.0 mmol) over 5 minutes. After 10 minutes more allow the reaction to warm to 0° C., then after 4 hours, to 20° C. for 2 h, and then to reflux for 0.5 hour. Cool the reaction to −78° C. and treat with neat 4-(N-methoxy-N-methylcarboxamido)1-piperidinecarboxylic acid tert-butyl ester (prepared as described in U.S. Pat. No. 5,134,139) (0.653 g, 2.40 mmol). Allow the reaction to warm to 20° C. After 16 h, treat the reaction with saturated $NH_4Cl/H_2O$ (2 mL) and water (10 mL) and extract with $CH_2Cl_2$ (2×20 mL). Dry the combined extracts ($Na_2SO_4$), concentrate under vacuum, and chromatograph over silica gel eluting initially with 10:90 ethyl acetate/hexane, and then 20:80 ethyl acetate/hexane, isolating the component with an $R_f$~0.35 in the latter system. Remove the unreacted guaiacol contaminant from a $CH_2Cl_2$ solution of the chromatographed material with a 1M NaOH/$H_2O$ wash to obtain the title compound as an oil (0.543 g, 55%).

Anal. Calc. for $C_{27}H_{45}NO_5Si$: C, 65.95; H, 9.22; N, 2.85. Found: C, 66.01; H, 9.15; N, 3.02. CIMS ($C_4$): m/z=492 (8%), 436 (100%), 392 (25%). IR (KBr): 2945, 2868, 1697, 1471, 1423, 1280, 1173 cm$^{-1}$. $^1$H NMR (CDCl$_3$): δ(ppm) 6.94 (3 H, m), 4.06 (2 H, bd), 3.84 (3 H. s), 3.23 (1 H, tt, J=11.2, 4.0 Hz), 2.85 (2 H, bt, J=12.2 Hz), 1.84 (2 H, dd, J=13.2 3.0 Hz), 1.59 (2 H, m), 1.45 (9 H, s), 1.30 (3 H, m), 1.12 (18 H, d, J=7.1 Hz). $^{13}$C NMR (CDCl$_3$): δ206.1, 154.7, 149.4, 148.8, 134.7, 124.1, 123.2, 120.8, 79.4, 61.6, 47.8, 43.3 (broad), 28.4, 27.8, 17.8, 12.8.

EXAMPLE 2C

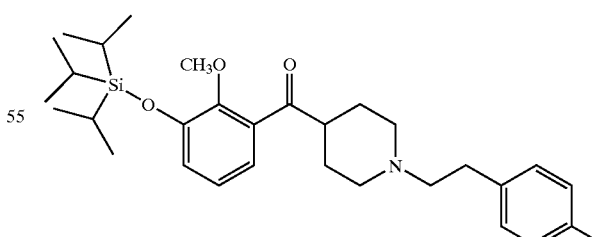

{1-[2-(4-Fluoro-phenyl)-ethyl]-piperidin-4-yl}-(2-methoxy-3-triisopropylsilanyloxy-phenyl)-methanone Stir and cool in an ice bath under nitrogen, 4-(2-methoxy-3-triisopropylsilanyloxy-benzoyl) -piperidine-1-carboxylic acid tert-butyl ester, Example 2B (5.71 g, 11.6 mmol) and add trifluoroacetic acid (30 mL). Remove the cold bath after 10 minutes. After 2 h, concentrate the reaction under vacuum at 40–45° C. and then pour into saturated aqueous NaHCO$_3$. Extract the basic layer with CH$_2$Cl$_2$ (2×200 mL), dry (Na$_2$SO$_4$), and concentrate under vacuum to an oil, which eventually solidifies to afford 4-(2-methoxy-3-triisopropylsilanyloxy-benzoyl) -piperidine.

Dissolve the crude amine from above in dry acetonitrile (60 mL), treat with diisopropylethylamine (4.9 mL, 28.2 mmol) and add 2-(4-fluorophenyl)ethyl-1-mesylate, (synthesis is described in U.S. Pat. No. 4,221,817) (3.07 g, 14.1 mmol). Heat the reaction at reflux under nitrogen for 24 hours, cool, treat with saturated aqueous NaHCO$_3$ (50 mL), and extract with CH$_2$Cl$_2$ (150 mL). The combined extracts were dried (MgSO$_4$) and concentrated under vacuum to an oil. Purify the product by column chromatography over silica gel, eluting with 30:70 ethyl acetate/hexane to give 4.72 g (80%) of oil (R$_f$~0.3 streaking).

Anal. Calc. for C$_{30}$H$_{44}$FNO$_3$Si: C, 70.13; H, 8.63; N, 2.73. Found: C, 70.03; H, 8.52; N, 2.88. CIMS (CH$_4$): m/z=514 (70%), 404 (100%). IR (neat): 2945, 2868, 1690, 1510, 1470, 1296, 1222, 956 cm$^{-1}$. $^1$H NMR (CDCl$_3$): δ(ppm) 7.17–7.11 (2 H, m), 6.97–6.91 (5 H), 3.84 (3 H, s), 3.08 (1 H, m), 2.97 (2 H, m), 2.76 (2 H, dd), 2.55 (2 H, dd), 2.10 (2 H, dt), 1.91 (2 1H, bd), 1.80–1.68 (2 H), 1.37–1.24 (3 H, m), 1.10 (18 H). $^3$C NMR (CDCl$_3$): δ206.6, 162.9. 159.7, 149.4, 148.7, 136.1, 135.0, 130.0, 129.9, 124.1, 123.0, 120.8, 115.2, 114.9, 61.5, 60.7, 53.2, 47.9, 32.9, 28.1, 17.9, 12.8. $^{19}$F NMR (CDCl$_3$): δ–118.061 (m).

EXAMPLE 2D

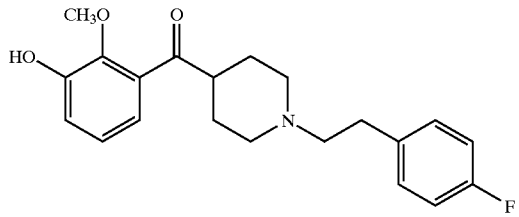

{1-[2-(4-Fluoro-phenyl)-ethyl]-piperidin-4-yl}-(3-hydroxy-2-methoxy-phenyl)-methanone Add to a solution of {1-[2-(4-fluoro-phenyl)-ethyl]-piperidin-4-yl}-(2-methoxy-3-triisopropylsilanyloxy-phenyl)-methanone, Example 2C (1.80 g, 3.50 mmol) in dry THF (5 mL) at ca. 20° C. under nitrogen, 1.0 M tetrabutylammonium fluoride in THF (4.55 mL, 4.55 mmol). After stirring 5 h, dilute the reaction with brine (100 mL) and extract with CH$_2$Cl$_2$ (3 ×75 mL). Dry the extracts (Na$_2$SO$_4$) and concentrate under vacuum. Purify the crude product by column chromatography over silica gel eluting initially with 50:50 ethyl acetate/hexane then 5:95 methanol/ethyl acetate giving the product as an oil (R$_f$~0.2 in ethyl acetate), which solidifies after standing. Triturate the solid with hexanes and recrystallize from hot ether (~30 mL) by cooling and concentrating under a nitrogen stream to ~10 mL. Collect the resulting slightly orange crystals to obtain 1.04 g (83 %) of the title compound, mp 100–101° C.

Anal. Calc. for C$_{21}$H$_{24}$FNO$_3$: C, 70.57; H, 6.77; N, 3.92. Found: C, 70.24; H, 6.72; N, 4.03. CIMS (CH$_4$): m/z=358 (100%), 338 (28%), 248 (96%). IR (KBr): 3437, 2957, 1684, 1510, 1221 cm$^{-1}$. $^1$H NMR (CDCl$_3$): δ(ppm) 7.14 (2 H, m), 7.06 (1H, s), 7.04 (1 H, d, J=2.1 Hz), 6.95 (3 H, m), 3.81 (3 H, s), 3.09 (1 H, m), 3.01 (2 H, m), 2.77 (2 H, dd, J=9.3, 11.0 Hz), 2.57(2 H, m), 2.14(2 H, dt, J=2.3, 11.4Hz), 1.82 (4 H, m). $^{13}$C NMR (CDCl$_3$): δ205.5, 163.0, 159.7. 149.3. 145.2, 135.9, 135.9, 132.8, 130.0. 129.9, 124.8. 120.1, 118.7, 115.2, 114.9, 62.8, 60.6, 53.2, 47.3, 32.7, 28.1. $^{19}$F NMR (CDCl$_3$): δ–17.913 (m).

EXAMPLE 2E

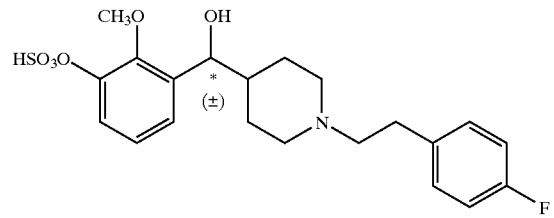

Sulfuric acid mono-(±)-[3-({1-[2-(4-fluoro-phenyl)-ethyl]-piperidin-4-yl}-hydroxy-methyl)-2-methoxy-phenyl]ester To a 7 mL glass screw cap tube add acetonitrile (200 μL), pyridine (200 μL), sulfur trioxide pyridine complex (20 mg, 130 μm) and {1-[2-(4-fluoro-phenyl)-ethyl]-piperidin-4-yl}-(3-hydroxy-2-methoxy-phenyl)-methanone, Example 2D (5.2 g, 15.2 μm). Place on a heating block and heat at 100° C. for 2 h. Cool and concentrate under vacuum (Savant concentrator), and dissolve residue in absolute ethanol (0.5 mL). Add NaBH$_4$ (30 mg) and then quench with acetic acid (100 μL). Dilute the reaction mixture 1/40 with 20:80 acetonitrile/buffer (0.1 7M acetic acid with 0.5M ammonium acetate) and analyze by LC/MS/MS (Zorbax RX, C8, 5 μm, 2.1×150 mm, buffer: 0.17M acetic acid and 0.05M ammonium acetate/acetonitrile; 75/25, Flow: 0.15 mL/min) t$_R$=6.83 min. CIDMS m/z=440 (M+H)$^+$. $^1$H NMR (300 MHz, DMSO-d$_6$)δ(ppm)=7.40 (d, 1H), 7.35 (t, 2H), 7.12 (t, 2H),7.00 (d, 1H), 6.95 (d, 2H), 4.95 (s, 1H), 4.63 (t, 1H), 3.79 (s, 3H), 3.50–2.40 (series of broad peaks, 9H), 1.90–1.40 (series of broad peaks, 5H). $^{13}$C NMR (75 MHz, DMSO-d$_6$)δ(ppm)=162.25, 159.95, 147.75, 145.59, 137.02, 130.05, 122.20, 121.5, 119.95, 115.05, 115.00. 69.03, 60.09, 57.00, 52.00, 33.33, 29.02, 26.02, 25.00, 24.05. $^{19}$F NMR (376 MHz, DMSO-d$_6$)δ(ppm)=–117.00.

The compounds of the present invention antagonize the effects of serotonin at the human 5-HT$_{2A}$-type serotonin receptor as shown by standard binding data. Conversely, the compounds of the present invention do not show any significant affinity at the following human receptors: dopamine—D$_2$; serotonin-5HT$_{2C}$; alpha adrenergic-α$_{1A}$ as shown by standard binding methods.

Receptor Binding Assays

Cells stably expressing the human homologs of the receptors (dopamine D$_{2L}$, serotonin 5HT$_{2A}$ and 5HT$_{2C}$, α$_{1A}$ adrenergic; cloned and expressed at Hoechst Marion Roussel; Grandy et al., 1989; Monsma et al., 1993; Schwinn et al. 1995) were grown; cell membranes were prepared, and kept frozen until used (Kongsamut et al., 1996). The relevance of these binding sites has been extensively discussed in the literature (see for example: Carlsson & Carlsson, 1990; Creese et al., 1976; Gorman & Vargas, 1995; Meltzer et al., 1989). All binding parameters were optimized at Hoechst Marion Roussel; ligand K$_d$s were determined using both saturation analysis (Scatchard) as well as kinetic analysis (association and dissociation rates). Each batch of membrane was validated by checking the ligand K$_d$, and rank order of potency of selected standard compounds. Assays for the serotonin $5HT_{2A}$ and dopamine $D_{2L}$ receptors were conducted at 37° C. in a Tris buffer containing salts (50 mM Tris Buffer, pH 7.7; 120 mM NaCl; 5 mM KCl; 2 mM $CaCl_2$; 1 mM $MgCl_2$), while the serotonin $5-HT_{2C}$ and α1A adrenergic receptor assays used a different buffer without salts (50 mM Tris, 4 mM $CaCl_2$ and 1% ascorbate, pH 7.4). Various binding parameters (ligand, ligand concentration, incubation times, ligand $K_d$s, displacing agent to define specific binding and tissue/cell line used) are summarized in the Table below (Closse et al., 1983; Hall et al., 1990; Leysen et al., 1977).

Membranes were rapidly thawed and diluted to an appropriate concentration (between 20–150 μg protein/assay point depending on receptor expression level) in Tris buffer and homogenized. Assay plates were incubated at 37° C. in an incubator for the times indicated. The assay was stopped by rapid filtration and washing (15 mL ice-cold 0.05M Tris buffer, pH 7.7) through Packard GF/B Unifilter plates (presoaked in 0.5% polyethyleneimine) using a Tomtec 96-well Cell Harvestor. Microscint scintillation cocktail (40 μl) were added and the filter plates were counted in a Packard Top Count scintillation counter. Data were analyzed to determine Ki's for compounds of interest (Prusoff & Cheng, 19). Table: Receptor Binding Parameters. All Scatchard analyses with the ligands below showed a single site; displacement of the ligands was assumed to be single site displacements.

Iloperidone binding to human and rat dopamine and serotonin receptors. *Eur J Pharmacol* 317: 417–423, 1996.
7. Leysen, J. E., Gommeren, W. & Laduron, P. M. Spiperone: A ligand of choice for neuroleptic receptors. *Biochem. Pharmacol.* 27: 307–328 (1977).
8. Meltzer, H. Y. Clinical studies on the mechanism of action of clozapine: the dopamine-serotonin hypothesis of schizophrenia. *Psychopharmacol* 99: S18–S27, 1989.
9. Monsma, F. J., Jr, Shen, Y., Ward, R. P., Flamblin, M. W. & Sibley, D. R. Cloning and expression of a novel serotonin receptor with high affinity for tricyclic psychotropic drugs. *Molec. Pharmacol.* 43: 320–327, 1993.
10. Schmidt, C., Sorensen S. M., Kehne, J. H., Carr, A. A. & Palfreyman, M. G. The role of $5TH_{2A}$ receptors in antipsychotic activity. *Life Sci.* 56: 2209–2222, 1995.
11. Schwinn, D. A., Johnston, G. I., Page, S. O. Mosley, M. J., Wilson, K. H., Worman, N. P., Campbell, S., Fidock. M. D., Furness, L. M., Parry-Smith, D. J., et al. Cloning and pharmacological characterization of human alpha-1 adrenergic receptors: sequence corrections and direct comparison with other species homologues. *J. Pharmacol. Exp. Ther.* 272:134–142, 1995.
12. Vargas, H. M.& Gorman, A. J. Vascular alpha-1 adrenergic receptor subtypes in the regulation of arterial pressure. *Life Sci.* 57: 2291–2308, 1995.

All of the forgoing references are incorporated herein by reference.

| receptor | ligand | ligand [conc.] (nM) | incubation time (min) | ligand Kd (nM) | non-specific binding | cell/tissue |
|---|---|---|---|---|---|---|
| human $D_{2L}$ | [$^3$H]N-methyl spiperone | 1 | 60 | 0.09 | 10 μM (−)eticlopride | CHO |
| human $5-HT_{2A}$ | [$^3$H]N-methyl spiperone | 1.5 | 40 | 0.92 | 30 μM methysergide | BHK |
| human $5-HT_{2C}$ | [$^3$H]mesulergine | 2 | 40 | 1.9 | 100 nM mianserin | CHO |
| human $α_{1A}$ | [$^3$H]prazosin | 1 | 40 | 0.19 | 10 μM phentolamine | CHO |

References

1. Carlsson, M., Carlsson, A. Interactions between glutamatergic and monoaminergic systems within the basal ganglia—implications for schizophrenia and Parkinson's disease. *Trends Neural Sci* 13: 272–276, 1990.
2. Closse, A. M. [$^3$H]Mesulergine, a selective ligand for $5HT_2$ receptors. *Life Sci.* 32: 2485–2495, 1983.
3. Creese, I., Burt, D. R. Snyder S. H. Dopamine receptor binding predicts clinical and pharmacological potencies of antischizophrenic drugs. *Science* 192: 481–483, 1976.
4. Grandy, D. K., Marchionni, M. A., Makam, H., Stofko, R. E., Alfano, M., Frothingham, L., Fischer, J. B., Burke-Howie, K. J., Bunzow, J. R., Server, A. C. and Civelli, O. Cloning of the cDNA and gene for a human $D_2$ dopamine receptor. *Proc. Nat. Acad. Sci. U.S.A.* 86: 9762–9766, 1989.
5. Hall, H., Wedel, I., Halldin, C., Kopp, J & Farde, L. Comparison of the in vitro Receptor Binding Properties of N-[$^3$H]Methylspiperone and [$^3$H]raclopride to Rat and Human Brain Membranes. *J. Neurochem.* 55: 2048–2057, 1990.
6. Kongsamut, S., Roehr, J. E., Cai, J., Hartman, H. B., Weissensee, P., Kerman, L. L., Tang, L. & Sandrasagra, A.

EXAMPLE 3

In vitro inhibition of [$^3$H]-Ligand binding to human $5-HT_{2A}$, $D_2$, $5HT_{2C}$ and $α_{1A}$ receptors

| Compound | $P_{app}$ (×10$^5$ cm/sec) at 5.4 μM | $P_{app}$ (×10$^5$ cm/sec) at 16 μM |
|---|---|---|
| Mannitol (standard) | 2.76 ± 0.23 | 2.76 ± 0.23 |
| Example 1H | 4.14 ± 0.69 | 3.44 ± 0.86 |

The compounds of this invention are capable of crossing the blood-brain barrier (BBB) as shown by their ability to penetrate across a membrane of a monolayer of bovine brain microvessel endothelial cells, an in vitro model for B3B permeability.

Bovine Brain Endothelial Cells (BBMEC)
TIransport Studies

The procedure was performed according to: Kenneth L. Audus et al., Brain Microvessel Endothelial Cell Culture System (Chapter 13) pp 239–258. *In Models for Assessing Drug Absorption and Metabolism,* Ronald T. Borchardt et al.

eds., Plenum Press, New York 1996, incorporated herein by reference. The test compounds are run at two concentrations (5.4 μM and 16 μM) and the apparent permeability coefficient is reported as $P_{app}$ in cm/sec and values reported as mean±standard deviation.

EXAMPLE 3

| Compound | In vitro BBMEC permeability | |
|---|---|---|
| | $P_{app}$ (×10$^5$ cm/sec) at 5.4 μM | $P_{app}$ (×10$^5$ cm/sec) at 16 μM |
| Mannitol (standard) | 2.76 ± 0.23 | 2.76 ± 0.23 |
| Example 1C | 4.14 ± 1.64 | 5.25 ± 0.95 |

What is claimed is:

1. A compound of Formula I

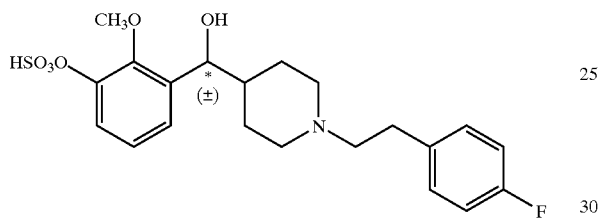

I or its pharmaceutically acceptable salts or enantiomers.

2. A pharmaceutical composition comprising the compound of claim 1 and a pharmaceutically acceptable carrier.

3. A method of making the compound of Formula I or its pharmaceutically acceptable salts,

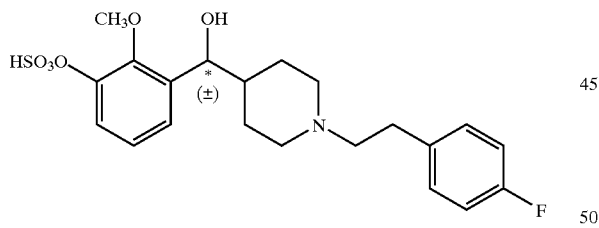

I comprising the steps of:
a) reacting a protected phenolic compound 7 with an alkyl lithium in an ethereal solvent

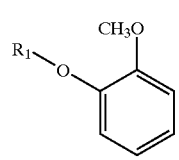

7 wherein $R_1$ is $Si(R_4)_3$; and
$R_4$ is $C_{1-4}$ alkyl, with a N-protected piperidine amide 8

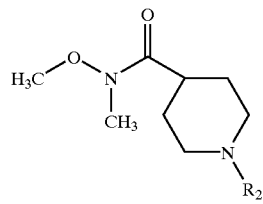

8 wherein
$R_2$ is aralkyl, $C_{1-2}$ alkyl or $COOR_5$ and
$R_5$ is $C_{1-6}$ alkyl, aryl or aralkyl, to produce compound 9;

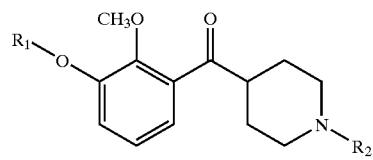

9 b) deprotecting the nitrogen of compound 9 to produce compound 10;

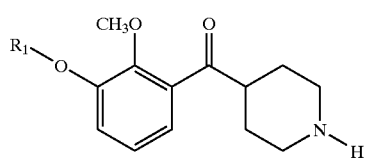

10 c) reacting compound 10 with compound 11

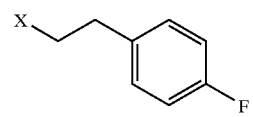

11 wherein X is a suitable leaving group, in the presence of an organic base and a polar aprotic solvent to produce compound 12;

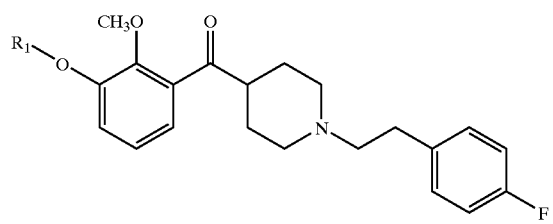

12 d) reacting compound 12 with a suitable desilylating agent to produce compound 13;

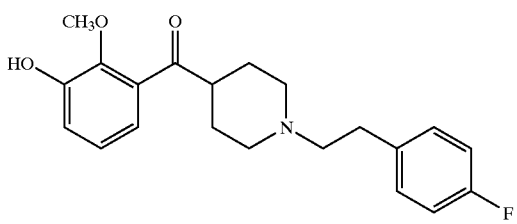

e) reacting compound 13 with a suitable sulfating reagent in an organic solvent to provide compound 14;

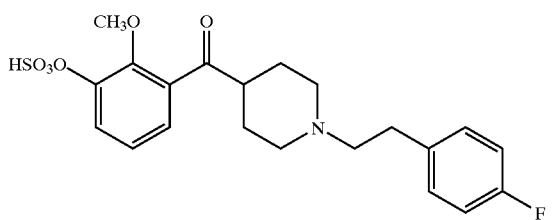

f) reacting compound 14 with a suitable reducing agent in a protic solvent to provide the compound of Formula I; and g) optionally reacting the compound of Formula I with an inorganic or organic acid to provide a pharmaceutically acceptable acid addition salt.

4. A method according to claim 3 wherein the alkyllithium is n-butyllithium.

5. A method according to claim 3 wherein the ethereal solvent is tetrahydrofuran.

6. A method according to claim 3 wherein the organic base is N-ethyldiisopropylamine.

7. A method according to claim 3 wherein the polar aprotic solvent is acetonitrile.

8. A method according to claim 3 wherein the desilylating reagent is tetra-N-butylammonium fluoride.

9. A method according to claim 3 wherein the ethereal solvent is tetrahydrofuran.

10. A method according to claim 3 wherein the sulfating reagent is sulfur trioxide pyridine complex.

11. A method according to claim 3 wherein the organic solvent is acetonitrile.

12. A method according to claim 3 wherein the reducing agent is sodium borohydride.

13. A method according to claim 3 wherein the protic solvent is ethanol.

14. A method of treating a patient suffering from a disease of the central nervous system comprising administering a compound according to claim 1 in an amount sufficient to antagonize the effects of serotonin at the $5HT_{2A}$ receptor.

15. A method according to claim 14 wherein the compound is sulfuric acid mono-(+)-[3-({1-[2-(4-fluoro-phenyl)-ethyl]-piperidin-4-yl}-hydroxy-methyl)-2-methoxy-phenyl]ester or a pharmaceutically acceptable salt thereof.

16. A method according to claim 14 wherein the compound is sulfuric acid mono-(−)-[3-({1-[2-(4-fluoro-phenyl)-ethyl]-piperidin-4-yl}-hydroxy-methyl)-2-methoxy-phenyl]ester or a pharmaceutically acceptable salt thereof.

17. A method for the treatment of schizophrenia comprising administering to a patient in need thereof a therapeutically sufficient amount of sulfuric acid mono-(±)-[3-({1-[2-(4-fluoro-phenyl)-ethyl]-piperidin-4-yl]-(hydroxy-methyl)-2-methoxy-phenyl]ester, or a pharmaceutically acceptable salt thereof.

18. A method for the treatment of anxiety comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

19. A method for the treatment of variant angina comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

20. A method for the treatment of anorexia nervosa comprising administering to a patient in need thereof, a therapeutically sufficient amount sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

21. A method for the treatment of Raynaud's phenomenon comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

22. A method for the treatment of intermittent claudication comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

23. A method for the treatment of fibromyalgia comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

24. A method for the treatment of coronary or peripheral vasospasms comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

25. A method for the treatment of cardiac arrhythmias comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

26. A method for the treatment of thrombotic illness comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

27. A method for the treatment extrapyramidal symptoms comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

28. A method for the treatment of depression comprising administering to a patient in need thereof, a therapeutically sufficient amount sulfuric acid mono-(±)-[3-({1-[2-(4- fluoro-phenyl)-ethyl]-piperidin-4-yl}-hydroxy-methyl)-2-methoxy-phenyl]ester, or a pharmaceutically acceptable salt thereof.

29. A method for the treatment of bipolar disorder comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

30. A method for the treatment of obsessive-compulsive disorders comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

31. A method for the treatment of insomnia comprising administering to a patient in need thereof, a therapeutically sufficient amount of sulfuric acid mono-(±)-(3-({1-[2-(4-fluoro-phenyl)-ethyl]-piperidin-4-yl}-hydroxy-methyl)-2-methoxy-phenyl]ester, or a pharmaceutically acceptable salt.

32. A method for the treatment of sleep apnea comprising administering to a patient in need thereof, a therapeutically sufficient amount of sulfuric acid mono-(±)-[3-({1-[2-(4-fluoro-phenyl)-ethyl]-piperidin-4-yl}-hydroxy-methyl)-2-methoxy-phenyl]ester, or a pharmaceutically acceptable salt thereof.

33. A compound of Formula II

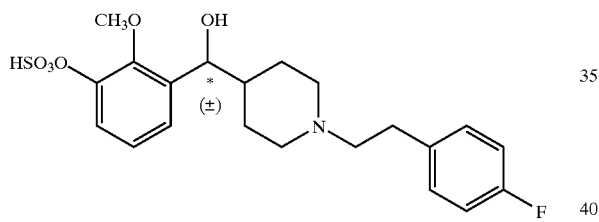

or a pharmaceutically acceptable salt thereof.

34. A pharmaceutical composition comprising the compound of claim 33 and a pharmaceutically acceptable carrier.

35. A method of making the compound of Formula II or its pharmaceutically acceptable salts,

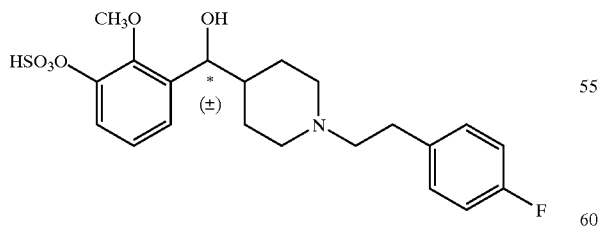

comprising the steps of:

a) reacting the diprotected compound 2, wherein Pg means a suitable protecting group with an alkali bicarbonate in an aqueous protic solvent

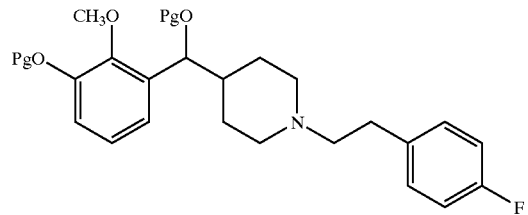

to produce compound 3;

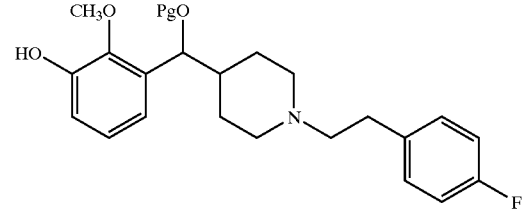

b) reacting compound 3 with a suitable sulfating reagent in an organic solvent to produce compound 4;

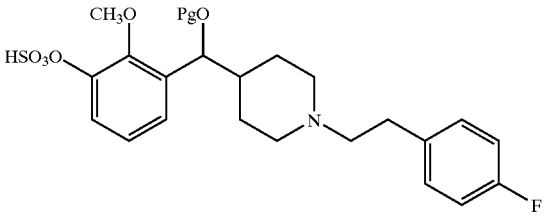

c) deprotecting compound 4 with an alkali carbonate in an aqueous protic solvent to provide the compound of Formula II; and d) optionally reacting the compound of Formula II with an inorganic or organic acid to provide a pharmaceutically acceptable acid addition salt.

36. A method according to claim 35 wherein the alkali bicarbonate is sodium bicarbonate.

37. A method according to claim 35 as in step a wherein the aqueous protic solvent is methanol-water.

38. A method according to claim 35 wherein the sulfating reagent is sulfur trioxide pyridine complex.

39. A method according to claim 35 wherein the organic solvent is acetonitrile.

40. A method according to claim 35 wherein the alkali carbonate is potassium carbonate.

41. A method according to claim 35 as in step c wherein the aqueous protic solvent is methanol-water.

42. A method of making sulfuric acid mono-(+)-[3-({1-[2-(4-fluoro-phenyl)-ethyl]-piperidin-4-yl}-hydroxy-methyl)-2-methoxy-phenyl]ester, comprising the steps of:

a) administering to a patient a therapeutically sufficient amount of (+)-α-(2,3-dimethoxyphenyl)1-[2-(4-fluorophenyl)ethyl]-4-piperidinemethanol; and b) isolating, from the patient sulfuric acid mono-(+)-[3-({1-[2-(4-fluoro-phenyl)-ethyl]-piperidin-4-yl}-hydroxy-methyl)-2-methoxy-phenyl]ester.

43. A method for the treatment of schizophrenia comprising administering to a patient in need thereof a therapeutically sufficient amount of sulfuric acid mono-(+)-[3-({1-[2-(4-fluoro-phenyl)-ethyl]-piperidin-4-yl]-(hydroxy-methyl)-2-methoxy-phenyl]ester, or a pharmaceutically acceptable salt thereof.

44. A method for the treatment of anxiety comprising administering to a patient in need thereof, a therapeutically sufficient amount of sulfuric acid mono-(+)-[3-({1-[2-(4-fluoro-phenyl)-ethyl]-piperidin-4-yl}-hydroxy-methyl)-2-methoxy-phenyl]ester, or a pharmaceutically acceptable salt thereof.

45. A method for the treatment of variant angina comprising administering to a patient in need thereof, a therapeutically sufficient amount of sulfuric acid mono-(+)-[3-({1-[2-(4-fluoro-phenyl)-ethyl]-piperidin-4-yl}-hydroxy-methyl)-2-methoxy-phenyl]ester, or a pharmaceutically acceptable salt thereof.

46. A method for the treatment of anorexia nervosa comprising administering to a patient in need thereof, a therapeutically sufficient amount sulfuric acid mono-(+)-[3-({1-[2-(4-fluoro-phenyl)-ethyl]-piperidin-4-yl}-hydroxy-methyl)-2-methoxy-phenyl]ester, or a pharmaceutically acceptable salt thereof.

47. A method for the treatment of Raynaud's phenomenon comprising administering to a patient in need thereof, a therapeutically sufficient amount of sulfuric acid mono-(+)-[3-({1-[2-(4-fluoro-phenyl)-ethyl]-piperidin-4-yl}-hydroxy-methyl)-2-methoxy-phenyl]ester, or a pharmaceutically acceptable salt thereof.

48. A method for the treatment of intermittent claudication comprising administering to a patient in need thereof, a therapeutically sufficient amount of sulfuric acid mono-(+)-[3-({1-[2-(4-fluoro-phenyl)-ethyl]-piperidin-4-yl}-hydroxy-methyl)-2-methoxy-phenyl]ester, or a pharmaceutically acceptable salt thereof.

49. A method for the treatment of fibromyalgia comprising administering to a patient in need thereof, a therapeutically sufficient amount of sulfuric acid mono-(+)-[3-({1-[2-(4-fluoro-phenyl)-ethyl]-piperidin-4-yl}-hydroxy-methyl)-2-methoxy-phenyl]ester, or a pharmaceutically acceptable salt thereof.

50. A method for the treatment of coronary or peripheral vasospasms comprising administering to a patient in need thereof, a therapeutically sufficient amount of sulfuric acid mono-(+)-[3-({1-[2-(4-fluoro-phenyl)-ethyl]-piperidin4-yl}-hydroxy-methyl)-2-methoxy-phenyl]ester, or a pharmaceutically acceptable salt thereof.

51. A method for the treatment of cardiac arrhythmias comprising administering to a patient in need thereof, a therapeutically sufficient amount of sulfuric acid mono-(+)-[3-({1-[2-(4-fluoro-phenyl)-ethyl]-piperidin-4-yl}-hydroxy-methyl)-2-methoxy-phenyl]ester, or a pharmaceutically acceptable salt thereof.

52. A method for the treatment of thrombotic illness comprising administering to a patient in need thereof, a therapeutically sufficient amount of sulfuric acid mono-(+)-[3-({1-[2-(4-fluoro-phenyl)-ethyl]-piperidin-4-yl}-hydroxy-methyl)-2-methoxy-phenyl]ester, or a pharmaceutically acceptable salt thereof.

53. A method for the treatment extrapyramidal symptoms comprising administering to a patient in need thereof, a therapeutically sufficient amount of sulfuric acid mono-(+)-[3-({1-[2-(4-fluoro-phenyl)-ethyl]-piperidin-4-yl}-hydroxy-methyl)-2-methoxy-phenyl]ester, or a pharmaceutically acceptable salt thereof.

54. A method for the treatment of depression comprising administering to a patient in need thereof, a therapeutically sufficient amount sulfuric acid mono-(+)-[3-({1-[2-(4-fluoro-phenyl)-ethyl]-piperidin-4-yl}-hydroxy-methyl)-2-methoxy-phenyl]ester, or a pharmaceutically acceptable salt thereof.

55. A method for the treatment of bipolar disorder comprising administering to a patient in need thereof, a therapeutically sufficient amount of sulfuric acid mono-(+)-[3-({1-[2-(4-fluoro-phenyl)-ethyl]-piperidin4-yl}-hydroxy-methyl)-2-methoxy-phenyl]ester, or a pharmaceutically acceptable salt thereof.

56. A method for the treatment of obsessive-compulsive disorders comprising administering to a patient in need thereof, a therapeutically sufficient amount of sulfuric acid mono-(+)-[3-({1-[2-(4-fluoro-phenyl)-ethyl]-piperidin-4-yl}-hydroxy-methyl)-2-methoxy-phenyl]ester, or a pharmaceutically acceptable salt thereof.

57. A method for the treatment of insomnia comprising administering to a patient in need thereof, a therapeutically sufficient amount of sulfuric acid mono-(+)-[3-({1-[2-(4-fluoro-phenyl)-ethyl]-piperidin-4-yl}-hydroxy-methyl)-2-methoxy-phenyl]ester, or a it pharmaceutically acceptable salt.

58. A method for the treatment of sleep apnea comprising administering to a patient in need thereof, a therapeutically sufficient amount of sulfuric acid mono-(+)-[3-({1-[2-(4-fluoro-phenyl)-ethyl]-piperidin-4-yl}-hydroxy-methyl)-2-methoxy-phenol]ester, or a pharmaceutically acceptable salt thereof.

59. A method as in any of claims 43 or 44–58 in which administering means administration of a prodrug to provide a therapeutically sufficient amount of sulfuric acid mono-(+)-[3-({1-[2-(4-fluoro-phenyl)-ethyl]-piperidin-4-yl}-hydroxy-methyl)-2-methoxy-phenyl]ester wherein the prodrug is (+)-α-(2,3-dimethoxyphenyl)-1-[2-(4-fluorophenyl)ethyl]-4-piperidinemethanol.

60. A compound of Formula III

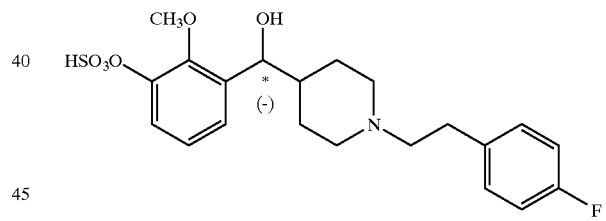

or a pharmaceutically acceptable salt thereof.

61. A pharmaceutical composition comprising the compound of claim 60 and a pharmaceutically acceptable carrier.

62. A method of making the compound of Formula III or its pharmaceutically acceptable salts,

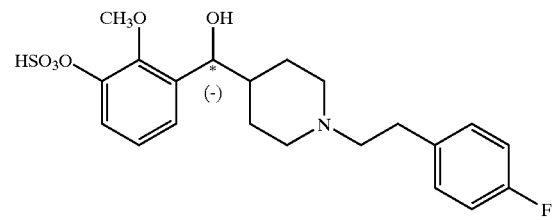

comprising the steps of:
  a) reacting the diprotected compound 2 wherein Pg means a suitable protecting group, with an alkali bicarbonate in/an aqueous protic solvent

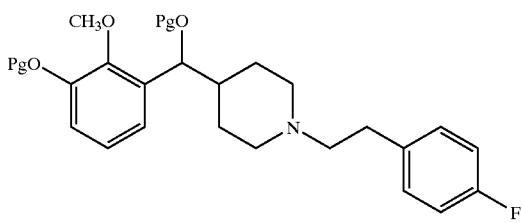

to produce compound 3;

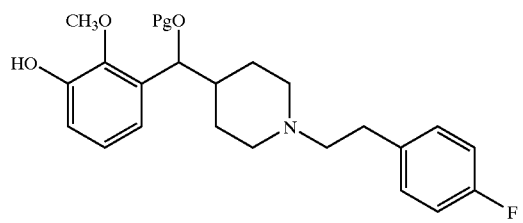

b) reacting compound 3 with a suitable sulfating reagent in an organic solvent to produce compound 4;

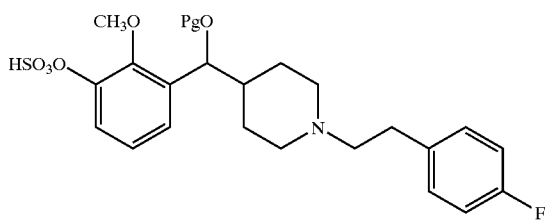

c) deprotecting compound 4 with an alkali carbonate in an aqueous protic solvent to to provide the compound of Formula III; and d) optionally reacting the compound of Formula III with an inorganic or organic acid to provide a pharmaceutically acceptable acid addition salt.

63. A method according to claim 62 wherein the alkali bicarbonate is sodium bicarbonate.

64. A method according to claim 62 as in step a wherein the aqueous protic solvent is methanol-water.

65. A method according to claim 62 wherein the sulfating reagent is sulfur trioxide pyridine complex.

66. A method according to claim 62 wherein the organic solvent is acetonitrile.

67. A method according to claim 62 wherein the alkali carbonate is potassium carbonate.

68. A method according to claim 62 as in step c wherein the aqueous protic solvent is ethanol-water.

69. A method of making sulfuric acid mono-(−)-[3-({1-[2-(4-fluoro-phenyl)ethyl]-piperidin-4-yl}-hydroxy-methyl)-2-methoxy-phenyl]ester, comprising the steps of:

a) administering to a patient a therapeutically effective amount of (−)-α-(2,3-dimethoxyphenyl)-1-[2-(4-fluorophenyl)ethyl]-4-piperidinemethanol; and b) isolating, from the patient sulfuric acid mono-(−)-[3-({1-[2-(4-fluoro-phenyl)-ethyl]-piperidin-4-yl}-hydroxy-methyl)-2-methoxy-phenyl]ester.

70. A method for the treatment of schizophrenia comprising administering to a patient in need thereof a therapeutically sufficient amount of sulfuric acid mono-(−)-[3-({1-[2-(4-fluoro-phenyl)-ethyl]-piperidin-4-yl]hydroxy-methyl)-2-methoxy-phenyl]ester, or a pharmaceutically acceptable salt thereof.

71. A method for the treatment of anxiety comprising administering to a patient in need thereof a therapeutically sufficient amount of sulfuric acid mono-(−)-[3-(({1-[2-(4-fluoro-phenyl)-ethyl]-piperidin-4-yl}-hydroxy-methyl)-2-methoxy-phenyl]ester, or a pharmaceutically acceptable salt thereof.

72. A method for the treatment of variant angina comprising administering to a patient in need thereof, a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester, or a pharmaceutically acceptable salt thereof.

73. A method for the treatment of anorexia nervosa comprising administering to a patient in need thereof, a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester, or a pharmaceutically acceptable salt thereof.

74. A method for the treatment of Raynaud's phenomenon comprising administering to a patient in need thereof, a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester, or a pharmaceutically acceptable salt thereof.

75. A method for the treatment of intermittent claudication comprising administering to a patient in need thereof, a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester, or a pharmaceutically acceptable salt thereof.

76. A method for the treatment of coronary or peripheral vasospasms comprising administering to a patient in need thereof, a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester, or a pharmaceutically acceptable salt thereof.

77. A method for the treatment of fibromyalgia comprising administering to a patient in need thereof, a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester, or a pharmaceutically acceptable salt thereof.

78. A method for the treatment of cardiac arrhythmias comprising administering to a patient in need thereof, a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester, or a pharmaceutically acceptable salt thereof.

79. A method for the treatment of thrombotic illness comprising administering to a patient in need thereof, a therapeutically sufficient amount of sulfuric acid mono-(−)-[3-({1-[2-(4-fluoro-phenyl)ethyl]-piperidin-4-yl}-hydroxy-methyl)-2-methoxy-phenyl]ester, or a pharmaceutically acceptable salt thereof.

80. A method for the treatment extrapyramidal symptoms comprising administering to a patient in need thereof, a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester, or a pharmaceutically acceptable salt thereof.

81. A method for the treatment of depression comprising administering to a patient in need thereof, a therapeutically sufficient amount of sulfuric acid mono-(−)-[3-({1-[2-(4- fluoro-phenyl)-ethyl]-piperidin-4-yl}-hydroxy-methyl)-2-methoxy-phenyl]ester, or a pharmaceutically acceptable salt thereof.

82. A method for the treatment of bipolar disorder comprising administering to a patient in need thereof, a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester, or a pharmaceutically acceptable salt thereof.

83. A method for the treatment of obsessive-compulsive disorders comprising administering to a patient in need thereof, a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester, or a pharmaceutically acceptable salt thereof.

84. A method for the treatment of insomnia comprising administering to a patient in need thereof, a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester, or a pharmaceutically acceptable salt thereof.

85. A method for the treatment of sleep apnea comprising administering to a patient in need thereof, a therapeutically sufficient amount of sulfuric acid mono-(−)-[3-({2-[2-(4-fluoro-phenyl)-ethyl]-piperidin-4-yl}-hydroxy-methyl)-2-methoxy-phenyl]ester, or a pharmaceutically acceptable salt thereof.

86. A method as in any of claims 69 or 70–85 in which administering means administration of a prodrug to provide a therapeutically sufficient amount of sulfuric acid mono-(−)-[3-({1-[2-(4-fluoro-phenyl)-ethyl]-piperidin-4-yl}-hydroxy-methyl)-2-methoxy-phenyl]ester wherein the prodrug is (+)-α-(2,3-dimethoxyphenyl)-1-[2-(4-fluorophenyl)ethyl]-4-piperidinemethanol.

\* \* \* \* \*

UNITED STATES PATENT AND TRADEMARK OFFICE
CERTIFICATE OF CORRECTION

PATENT NO.    : 6,465,490 B1
DATED         : October 15, 2002
INVENTOR(S)   : Ronald C. Bernotas et al.

It is certified that error appears in the above-identified patent and that said Letters Patent is hereby corrected as shown below:

Title page, Item [54] and Column 1, line 1,
Title, reads "SULFURIC ACID MONO-[3({1-[2-......" and should read
-- SULFURIC ACID MONO-[3-({1-[2-... --.

Column 1,
Line 23, reads "(+)-α-(2.3-Dimethoxyphenyl)-1-[2-(4-fluorophenyl)..." and should read -- (+)-α-(2,3-Dimethoxyphenyl)-1-[2-(4-fluorophenyl --.
Line 44, reads "with neuroleptic therapy, depression. bipolar disorders" and should read -- with neuroleptic therapy, depression, bipolar disorders, --.
Line 60, reads "as $5TH_{2A}$ receptor" and should read -- as $5HT_{2A}$ receptor --.

Column 2,
Line 4, reads "the $5TH_{2A}$ receptor and" and should read -- the $5HT_{2A}$ receptor, and --.
Line 11, reads "dimethoxyphenyl)1-[2-(4-fluorophenyl)ethyl]-4-" and should read -- dimethoxyphenyl)-1-[2-(4-fluorophenyl)ethyl]-4- --.

Column 3,
Line 41, reads "include hydrochloric, hydrobroinic, sulfixic and phosphoric" and should read -- include hydrochloric, hydrobromic, sulfuric and phosphoric --.

Column 5,
Line 24, reads "mental acts (c.g., praying, counting, repeating words" and should read -- mental acts (e.g., praying, counting, repeating words --.

Column 7,
Line 31, reads "piperidinemethanol as described in Heath, F.G. et al, *J. Am.*" and should read -- piperidinemethanol as described in Heath, T.G. et al, *J.Am.* --.
Line 63, reads "chlorosulfonic acid with acid or base. pyridine sulfur trioxide" and should read -- chlorosulfonic acid with acid or base, pyridine sulfur trioxide --.

Column 9,
Line 47, reads "Step 1: Guiacol, the compound 6, available from the" and should read -- Step B1: Guiacol, the compound 6, available from the --.
Line 51, reads "derivative 7. Suitable trialkylsilyl halides are compounds" and should read -- derivative 7. Suitable trialkylsilyl halides, are compounds --.

UNITED STATES PATENT AND TRADEMARK OFFICE
CERTIFICATE OF CORRECTION

PATENT NO. : 6,465,490 B1
DATED : October 15, 2002
INVENTOR(S) : Ronald C. Bernotas et al.

It is certified that error appears in the above-identified patent and that said Letters Patent is hereby corrected as shown below:

Column 10,
Line 13, reads "tetrahydrofuiran being the preferred solvent. This results in" and should read -- tetrahydrofuran being the preferred solvent. This results in --.
Line 38, reads "triethylamine. lutidine and N-ethyldiisopropylamine, with" and should read -- triethylamine, lutidine and N-ethyldiisopropylamine, with --.

Column 11,
Line 2, reads "appropriate organic solvents are benzene. toluene." and should read -- appropriate organic solvents are benzene, toluene, --.

Column 12,
Line 57, reads "Walbine S. et al., *Tetrahedron Assymetry.* 1992, 3," and should read -- Walbine S. et al., *Tetrahedron Asymmetry,* 1992, 3 --.
Line 60, reads "diphenyl1-substituted pyrrolidino[1,2-c]-1,3,2-oxazaboroles" and should read -- diphenyl-1-substituted pyrrolidino[1,2-c]-1,3,2-oxazaboroles --.
Line 61, reads "and (R) or (S)-3,3-di-β-naphthyl1-substituted pyrrolidino[1," and should read -- and (R) or (S)-3,3-di-β-naphthyl-1-substituted pyrrolidino[1, --.

Column 15,
Line 21, reads "collision-induced dissociation mass spectrum. "NMR"" and should read -- collision-induced dissociation mass spectrum, "NMR" --.
Line 24, reads "of the distance which the sample migrates (on TI,C) as" and should read -- of the distance which the sample migrates (on TLC) as --.

Column 16,
Line 30, reads "through silica gel eluting with 1:1 MeOHI/CHCl$_3$." and should read -- through silica gel eluting with 1:1 MeOH/CHCl$_3$. --.

Column 17,
Line 35, reads "phenyl)-ethyl]-piperidin4-yl}-(3-hydroxy-2-" and should read -- phenyl)-ethyl]-piperidin-4-yl}-(3-hydroxy-2- --.
Line 56, reads "(+)1-[2-(4-Fluorophenyl-)ethyl]-α-(3-hydroxy-2-" and should read -- (+)-1-[2-(4-Fluorophenyl-)ethyl]-α-(3-hydroxy-2- --.

Column 19,
Line 13, reads "Sulfuric acid mono-(+)-[3-({1-[2-(4-fluoro-phenyl)-" and should read -- Sulfuric acid mono-(+)-[3-(-{1-[2-(4-fluoro-phenyl)- --.
Line 32, reads "2H), 7.12(t, 2H), 7.00 (d, 1H), 6.95 (d, 2H), 4.63 (t, 1H)," and should read -- 2H), 7.12(t, 2H), 7.00 (d, 1H), 6.95 (d, 2H), 4.95 (s,1H), 4.63 (t, 1H), --.

UNITED STATES PATENT AND TRADEMARK OFFICE
CERTIFICATE OF CORRECTION

PATENT NO. : 6,465,490 B1
DATED : October 15, 2002
INVENTOR(S) : Ronald C. Bernotas et al.

It is certified that error appears in the above-identified patent and that said Letters Patent is hereby corrected as shown below:

Column 19 cont'd,
Line 64, reads "anal. Calc. For $C_{16}H_{28}O_2Si$: C,68,50;H, 10.08. Found: C," and
should read -- Anal. Calc. For $C_{16}H_{28}O_2Si$: C, 68,50; H, 10.08. Found: C, --.
Line 66, reads "IR (KBr): 2945, 2868, 1504, 1458, 1267, 920, 745 cm$^{-1}$. $^1$H" and
should read -- IR (KBr): 2945, 2868, 1504, 1458, 1282, 1267, 920, 745 cm$^{-1}$. $^1$H --.
Line 67, reads "NMR (CDCl$_3$): δ6.90-6.75(4 H), 3.79 (3 H, m), 1.09 (6 H," and
should read -- NMR (CDCl$_3$): δ 6.90-6.75 (4 H), 3.79 (3 H, s), 1.32-1.19(1 H, m), 1.09 (6 H --.

Column 20,
Line 20, reads "of 2-methoxyl-(triisopropylsilyloxy)benzene, Example 2A" and
should read -- of 2-methoxy-l-(triisopropylsilyloxy)benzene, Example 2A --.
Line 26, reads "4-(N-methoxy-N-methylcarboxamido)1-" and
should read -- 4-(N-methoxy-N-methylcarboxamido)-1 --.
Line 40, reads "Found: C, 66.01; H, 9.15; N, 3.02. CIMS ($C_4$): m/z=492" and
should read -- Found: C, 66.01; H, 9.15; N,3.02. CIMS ($CH_4$): m/z=492 --.
Line 43, reads "6.94 (3 H, m), 4.06 (2 H, bd), 3.84 (3 H.s), 3.23 (1 H, tt," and
should read -- 6.94 (3 H, m), 4.06 (2 H, bd), 3.84 (3 H, s), 3.23 (1 H, tt --.
Line 45, reads "J=13.2 3.0 Hz), 1.59 (2H, m), 1.45 (9H, s), 1.30 (3H, m)" and
should read -- J=13.2, 3.0 Hz), 1.59 (2 H, m), 1.45 (9 H, s), 1.30 (3 H, m) --.

Column 21,
Line 26, reads "2.10 (2 H, dt), 1.91 (2 1H, bd), 1.80-1.68 (2 H), 1.37-1.24" and
should read -- 2.10 (2 H, dt), 1.91 (2 H, bd), 1.80-1.68 (2 H), 1.37-1.24 --.
Line 27, reads "(3 H, m), 1.10 (18 H). $^3$C NMR (CDCl$_3$): δ206.6, 162.9." and
should read -- (3 H, m), 1.10 (18 H). $^{13}$C NMR (CDCl$_3$): δ 206.6, 162.9. --.

Column 22,
Line 3, reads "m). $^{13}$C NMR (CDCl$_3$): δ205.5, 163.0, 159.7. 149.3. 145.2," and
should read -- m). $^{13}$C NMR (CDCl$_3$): δ 205.5, 163.0, 159.7, 149.3, 145.2, --.
Line 6, reads "(CDCl$_3$): δ-17.913 (m)." and should read -- (CDCl$_3$): δ -117.913 (m). --.
Line 51, reads "dopamine-$D_2$; serotonin-SHT$_{2c}$; alpha adrenergic-$α_{1A}$ as" and
should read -- dopamine-$D_2$; serotonin-5HT$_{2c}$; alpha adrenergic-$α_{1A}$ as --.
Line 57, reads "Grandy et al, 1989; Monsma et al., 1993; Schwinn et al." and
should read -- Grandy et al., 1989; Monsma et al., 1993; Schwinn et al., --.

UNITED STATES PATENT AND TRADEMARK OFFICE
CERTIFICATE OF CORRECTION

PATENT NO. : 6,465,490 B1
DATED : October 15, 2002
INVENTOR(S) : Ronald C. Bernotas et al.

It is certified that error appears in the above-identified patent and that said Letters Patent is hereby corrected as shown below:

Column 23,
Line 52, reads "3. Creese, I., Burt, D. R. Snyder S. H. Dopamine receptor" and should read -- 3. Creese, I., Burt, D. R., Snyder S. H. Dopamine receptor --.

Column 24,
Line 10, reads "9. Monsma, F. J., Jr, Shen, Y., Ward, R. P., Flambin, M. W." and should read -- 9. Monsma, F. J., Jr, Shen, Y., Ward, R. P., Hamblin, M. W. --.
Line 17, reads "11. Schwinn, D. A., Johnston, G. I., Page, S. O. Mosley, M." and should read -- 11. Schwinn, D. A., Johnston, G. I., Page, S. O., Mosley, M. --.

The Table at Lines 50 through Lines 54 should be deleted and insert therefor the following Table.

| Compound | $5HT_{2A}$ ($K_i$ $\mu M$) | $D_2$ ($K_i$ $\mu M$) | $5HT_{2C}$ ($K_i$ $\mu M$) | $\alpha_{1A}$ ($K_i$ $\mu M$) |
|---|---|---|---|---|
| Example 1H | 0.16 | >1.0 | >1.0 | >1.0 |

Column 25,
Line 59, reads "an in vitro model for B3B" and should read -- an in vitro model for BBB --.
The Table at Line 10 thru 15 reads:

| Compound | $P_{app}$(x$10^5$ cm/sec) at 5.4 $\mu M$ | $P_{app}$(x$10^5$ cm/sec) at 16 $\mu M$ |
|---|---|---|
| Mannitol (standard) | 2.76 ± 0.23 | 2.76 ± 0.23 |
| Example 1C | 4.14 ± 1.64 | 5.25 ± 0.95 | and should read:

| Compound | $P_{app}$(x$10^5$ cm/sec) at 5.4 $\mu M$ | $P_{app}$(x$10^5$ cm/sec) at 16 $\mu M$ |
|---|---|---|
| Mannitol (standard) | 2.76 ± 0.23 | 2.76 ± 0.23 |
| Example 1H | 4.14 ± 0.69 | 3.44±0.86 |

UNITED STATES PATENT AND TRADEMARK OFFICE
CERTIFICATE OF CORRECTION

PATENT NO.     : 6,465,490 B1
DATED          : October 15, 2002
INVENTOR(S)    : Ronald C. Bernotas et al.

It is certified that error appears in the above-identified patent and that said Letters Patent is hereby corrected as shown below:

Column 31,
Line 44, reads "mono-(+)-[3-({1-[2-(4-fluoro-phenyl)-ethyl]-piperdin4-" and
should read -- mono-(+)-[3-({1-[2-(4-fluoro-phenyl)-ethyl]-piperdin-4- --.

Column 33,
Line 41, reads "aqueous protic solvent to to provide the compound of" and
should read -- aqueous protic solvent to provide the compound of --.

Column 34,
Line 6, reads "administering to a patient in need thereof a therapeutically" and
should read -- administering to a patient in need thereof, a therapeutically --.
Line 7, reads "sufficient amount of sulfuric acid mono-(-)-3-(({1-[2-(4-" and
should read -- sufficient amount of sulfuric acid mono-(-)-3-({1-[2-(4- --.

Column 36,
Line 6 reads "sufficient amount of sulfuric acid mono-(-)-3-({2-[2-(4-" and
should read -- sufficient amount of sulfuric acid mono-(-)-3-({1-[2-(4- --.

Signed and Sealed this

Seventh Day of October, 2003

JAMES E. ROGAN
*Director of the United States Patent and Trademark Office*